(12) United States Patent
Weinstock et al.

(10) Patent No.: US 11,746,321 B2
(45) Date of Patent: Sep. 5, 2023

(54) METHODS OF CLONING NUCLEIC ACIDS OR PRODUCING PROTEINS IN A LOW ENDOTOXIN ORGANISM

(71) Applicant: Codex DNA, Inc., San Diego, CA (US)

(72) Inventors: Matthew T Weinstock, San Diego, CA (US); Daniel G. Gibson, Carlsbad, CA (US); Daniel Strimling, La Jolla, CA (US)

(73) Assignee: Telesis Bio Inc., San Diego, CA (US)

( * ) Notice: Subject to any disclaimer, the term of this patent is extended or adjusted under 35 U.S.C. 154(b) by 35 days.

(21) Appl. No.: 17/212,926

(22) Filed: Mar. 25, 2021

(65) Prior Publication Data

US 2021/0284954 A1 Sep. 16, 2021

Related U.S. Application Data

(62) Division of application No. 16/154,618, filed on Oct. 8, 2018, now Pat. No. 10,968,496.

(60) Provisional application No. 62/588,755, filed on Nov. 20, 2017.

(51) Int. Cl.
| | | |
|---|---|---|
| *C12N 1/20* | (2006.01) | |
| *C12N 15/74* | (2006.01) | |
| *C12N 9/10* | (2006.01) | |
| *C12R 1/63* | (2006.01) | |

(52) U.S. Cl.
CPC ............ *C12N 1/205* (2021.05); *C12N 9/1029* (2013.01); *C12N 15/74* (2013.01); *C12R 2001/63* (2021.05)

(58) Field of Classification Search
None
See application file for complete search history.

(56) References Cited

U.S. PATENT DOCUMENTS

| 10,377,997 B1 * | 8/2019 | Weinstock ..... C12Y 207/07006 |
| 2010/0112002 A1 | 5/2010 | Lien et al. |
| 2010/0272758 A1 | 10/2010 | Woodard et al. |
| 2013/0230555 A1 | 9/2013 | Trent et al. |
| 2014/0221251 A1 | 8/2014 | Bramhill et al. |
| 2014/0328880 A1 | 11/2014 | Lien et al. |
| 2016/0228523 A1 | 8/2016 | Newman |

FOREIGN PATENT DOCUMENTS

WO  WO 2007/084633 A2  7/2007

OTHER PUBLICATIONS

Chica et al. Curr Opin Biotechnol. Aug. 2005;16(4):378-84. (Year: 2005).
International Search Report dated Dec. 26, 2018, regarding PCT/US2018/054883.
Kizer et al. Appl Environ Microbiol. May 2008;74(10):3229-41. (Year: 2008).
Lee et al. Vibrio natriegens, a new genomic powerhouse. bioRxiv Jun. 12, 2016, pp. 1-30 (Year: 2016).
Prather et al. Curr Opin Biotechnol. Oct. 2008;19(5):468-74. (Year: 2008).
Singh et al. Curr Protein Pept Sci. 2017, 18, 1-11 (Year: 2017).
Weinstock et al. Nat Methods. Oct. 2016;13(10):849-51 (Year: 2016).
EP Extended European Search Report in European Application No. EP18878155, dated Nov. 12, 2021, 12 pages.
Lee et al., "Vibro natriegens, a new genomic powerhouse", bioRxiv, Jun. 2016, 30 pages.
Triana et al., "Multiplex Genome Editing by Natural Transformation (MuGENT) for Synthetic Biology in Vibrio natriegens", ACS Synthetic Biology, Sep. 20417, 6(9):1650-1655.
Weinstock et al., "Vibrio natriegens as a fast-growing host for molecular biology", Nature Methods, Oct. 2016,13(10):849-851.
Wiegand et al., "Cell-free Protein Expression Using the Rapidly Growing Bacterium emVibrio natriegens /em", Journal of Visualized Experiments, Jan. 2019, 379159495(145):59495.

* cited by examiner

*Primary Examiner* — Christian L Fronda
(74) *Attorney, Agent, or Firm* — DLA Piper LLP (US)

(57) ABSTRACT

The invention provides engineered *Vibrio* sp. organisms that comprise a genetic modification to either or both of the lpxL and/or lpxM genes. The organisms score substantially lower in an in vitro endotoxin assay versus the unmodified or wild type organism. The organisms preserve substantially the growth rate of the corresponding unmodified organisms. The organisms can also have an exogenous nucleic acid cloned in the organism, or an exogenous nucleic acid encoding a protein, polypeptide, or peptide expressed by the organism, and optionally secreted from the organism.

18 Claims, 8 Drawing Sheets
Specification includes a Sequence Listing.

| Strain | Media | Specific growth rate (hr-1) | |
|---|---|---|---|
| | | Flower well | Round bottom well |
| E. coli BL21(DE3) | LB media | 0.193 | 0.597 |
| | LBv2 media | 0.471 | 0.434 |
| E. coli ClearColi® BL21(DE3) | LB media | 0.106 | 0.16 |
| | LBv2 media | 0.089 | 0.149 |
| V. natriegens (wt) | LBv2 media | 0.758 | 0.903 |
| V. natriegens (ΔlpxL, ΔlpxM) | LBv2 media | 0.645 | 0.698 | ing an encoded exogenous protein. In the methods the

METHODS OF CLONING NUCLEIC ACIDS OR PRODUCING PROTEINS IN A LOW ENDOTOXIN ORGANISM

CROSS-REFERENCE TO RELATED APPLICATIONS

This application is a divisional application of U.S. application Ser. No. 16/154,618 filed Oct. 8, 2018, now issued as U.S. Pat. No. 10,968,496; which claims the benefit under 35 USC § 119(e) to U.S. Application Ser. No. 62/588,755 filed Nov. 20, 2017. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing text file, named CODEX2110-2_ST25.txt, was created on May 25, 2021 and is 17,694 bytes in size. The file can be accessed using Microsoft Word on a computer that uses Windows OS.

BACKGROUND OF THE INVENTION

Field of the Invention

The invention relates generally to recombinant *Vibrio* sp. organisms having low levels of endotoxin versus a wild type organism while maintaining high levels of exogenous nucleic acid and protein production.

Background Information

The gram-negative bacterium *E. coli* serves as an industrial host for the production of many therapeutic recombinant proteins of pharmaceutical interest (e.g., recombinant human insulin). While *E. coli* has been used in pharmaceutical production processes since the dawn of biotech in the 1970s, one key disadvantage of this host is its production of lipopolysaccharides (LPS). Like most gram-negative bacteria *E. coli* have an outer membrane containing the potent immunostimulatory molecule lipopolysaccharide (LPS). These LPS molecules (also known as endotoxin) make up a significant portion of the outer membrane of gram-negative bacteria. These molecules are composed of three main parts: a Lipid A moiety (highly conserved among gram-negative species), a core oligosaccharide (mostly conserved), and an O-antigen polysaccharide (variable between organisms).

The immune system of vertebrates (including humans) has evolved to detect these LPS molecules and trigger an immunogenic reaction in response to their presence. Humans are very sensitive to endotoxin, which can trigger a systemic inflammatory response (or immune reaction) that can lead to organ failure, shock, and even death. As a result, biologics produced in *E. coli* are required to undergo intensive purification and quality control analyses to ensure the removal of these molecules from any injectable biologics. There are various manners of removing endotoxins that contaminate biologics and other products of interest produced in gram-negative organisms such as *E. coli*. These methods generally involve removing the endotoxin from the product by ultrafiltration, passing it through activated carbon, washing with surfactants, or anion-exchange chromatography. These methods are expensive and time consuming, and add additional time/cost to downstream processing and diminish product yield.

It would therefore be highly desirable to have an organism for the production of biologics and other molecules of interest having a lipopolysaccharide that causes a substantially reduced or eliminated immunological response in mammals, thereby eliminating much of the need for these expensive and time consuming processes to remove lipopolysaccharides and also making products made by the organisms safer for human and animal use.

SUMMARY OF THE INVENTION

The invention provides engineered or recombinant *Vibrio* sp. organisms having a genetic modification of the genes lpxL and/or lpxM. In various embodiments either one or both of the genes are genetically modified or deleted. The organisms can optionally have an exogenous nucleic acid, for cloning the exogenous nucleic acid or for expressing or producing an encoded exogenous protein or peptide. The recombinant organisms produce low amounts of endotoxin compared to a corresponding organism not comprising the genetic modification(s), which can be measured using an in vitro endotoxin assay. Therefore, molecules synthesized in or harvested from the organism present a much lower risk of endotoxicity in humans and other mammals since they will not be contaminated with endotoxin. The recombinant organisms also retain a high rate of growth and continue to be culturable even though they comprise the one or more genetic modifications. The organisms are therefore highly useful for the production of biologics, proteins, single domain antibodies, nucleic acids, and other therapeutic molecules or other molecules of interest.

The invention also provides methods of cloning a nucleic acid or of producing a protein. The methods involve culturing a *Vibrio* sp. organism having a genetic modification to the lpxL and/or lpxM gene(s). The organism optionally also has an exogenous nucleic acid sequence, which is for cloning the exogenous nucleic acid sequence or for expressing an encoded exogenous protein. In the methods the organism produces or contains substantially less endotoxin compared to a corresponding organism not comprising the genetic modification and cultivated under the same conditions. The recombinant *Vibrio* sp. organism also exhibits a growth rate of at least 60% of the growth rate of the corresponding organism when cultivated under the same conditions.

In a first aspect the invention provides a recombinant *Vibrio* sp. organism having a genetic modification of the lpxL gene or the lpxM gene. The organism has or produces substantially less endotoxin compared to a corresponding organism not having the genetic modification and cultivated under the same conditions. The recombinant *Vibrio* sp. organism can exhibit a growth rate of at least 60% of the growth rate of the corresponding organism when cultivated under the same conditions. In any of the embodiments the organism can also contain an exogenous nucleic acid for the production of the exogenous nucleic acid or for the production of an encoded exogenous protein or peptide.

In one embodiment the genetic modification is selected from a deletion, a mutation, an attenuation, a disruption, an inactivation, or a downregulation of the lpxL or lpxM genes. The organism can have an outer membrane having a modified lipopolysaccharide component. In one embodiment the organism does not have a genetic modification in any gene selected from the group consisting of: gutQ, kdsD, pagP, and lpxP. In one embodiment the organism has a growth rate of at least 70% the growth rate of a corresponding unmodified or wild type *Vibrio* sp. organism under identical conditions, or can have a growth rate as otherwise disclosed herein. In one embodiment the organism has an average endotoxin level of less than 1 EU/ml measured in an in vitro assay. The organism can have a doubling time of 55-70 minutes at 30° C. The growth rate can be measured over a period of 8 hours or over a period of 12 hours. In a specific embodiment the genetic modification is a deletion and the organism is of the genus *Vibrio*, e.g., *Vibrio natriegens*.

In a specific embodiment the *Vibrio* sp. organism of the invention has a growth rate of at least 60% the growth rate of a wild type *Vibrio* sp. under the same growth conditions, and has an endotoxin level of less than 1 EU/ml, and a specific growth rate of at least 0.60 or 0.60-0.72 at 30° C. in LBv2 media. The organism can also have an exogenous nucleic acid for the cloning or production of the exogenous nucleic acid or for the production of an encoded heterologous protein or peptide.

In another aspect the invention provides a recombinant *Vibrio* sp. organism having an outer membrane having a modified lipopolysaccharide versus a wild type organism. The modified lipopolysaccharide can have a lipid component with a reduced number of acyl chains versus the lipid component in the wild-type organism. The recombinant organism can score substantially lower in an in vitro endotoxin assay versus the wild type organism. The recombinant organism can be any described herein that has the stated attributes.

In one embodiment the engineered *Vibrio* sp. organism of the invention has a modified LPS having a pentaacylated Lipid A. The organism can have a genetic modification to the lpxL or lpxM genes. The organism can have less than 50% of the endotoxicity of an unmodified *Vibrio* sp. organism, as measured in an in vitro LPS detection assay. In another embodiment the organism has less than 5% of the endotoxicity of an unmodified *Vibrio* sp. organism, as measured in an in vitro LPS detection assay. And in yet another embodiment the organism has less than 1% of the endotoxicity of a wild type *E. coli*, as measured in an in vitro LPS detection assay.

In one aspect, the invention provides a *Vibrio* sp. organism having less than 1% of the endotoxicity of a modified *E. coli* organism that comprises the genetic deletions ΔgutQ, ΔkdsD, ΔlpxL, ΔlpxM, ΔpagP, ΔlpxP, and ΔeptA, as measured in an in vitro LPS detection assay. In any of the embodiment the organism can be *Vibrio natriegens*.

In another aspect the invention provides methods of cloning a nucleic acid or of producing a protein, polypeptide, or peptide. The methods involve culturing a *Vibrio* sp. organism described herein, and harvesting the cloned nucleic acid or the protein or peptide produced by the organism. In one embodiment the organism has an exogenous nucleic acid that is cloned or amplified by the organism. In another embodiment the organism has an exogenous nucleic acid encoding a protein, polypeptide, or peptide produced or expressed by the organism, and optionally secreted from the organism. The organism can be any described herein and can have any of the attributes of organisms described herein.

Section heading or sub-headings are provided solely for the convenience of the reader, and do not denote a departure from discussion or necessarily an entirely new subject matter area. Any subject matter can be discussed or disclosed under any section heading or sub-heading.

BRIEF DESCRIPTION OF THE DRAWINGS

FIG. 2B provides an illustration of Lipid IV(A).

FIG. 3B presents the data in tabular format.

FIG. 7B is a graphical illustration of the ln(biomass) v. time. FIG. 7C is a graphical illustration of the linear portion of the graph in FIG. 7B.

DETAILED DESCRIPTION OF THE INVENTION

Figure 1:
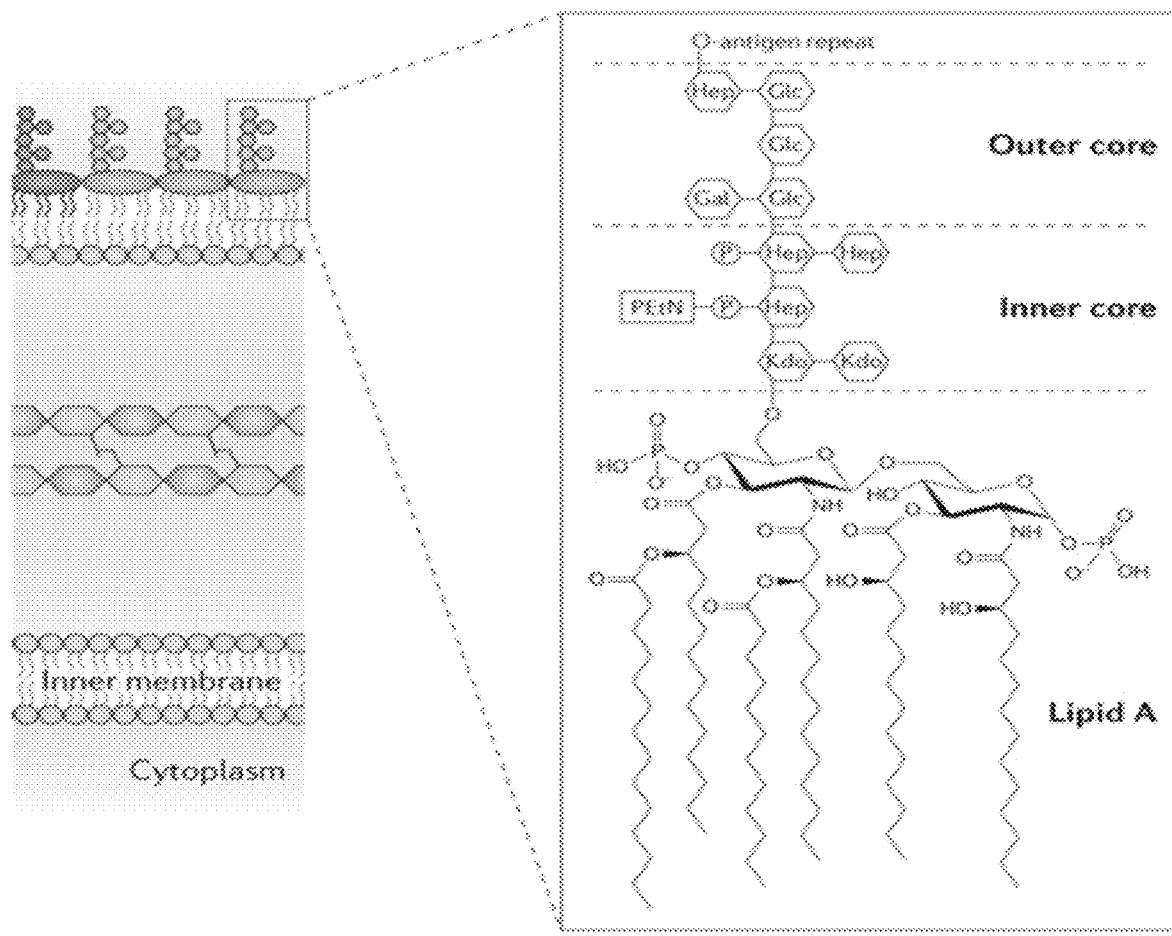
FIG. 1 provides an illustration of a membrane of a gram negative bacteria. The outer membrane is expanded for illustration of membrane components, including the Lipid A component (Okuda S., et al., Nature Reviews Microbiology, (2016) 14: 337-345).

The present invention provides a recombinant or engineered *Vibrio* sp. organism that has one or more genetic modifications affecting the lipopolysaccharide (LPS) component of its outer membrane, and the organism produces or contains substantially less endotoxin or immune-stimulatory LPS (or endotoxin) substances than the corresponding unmodified or wild-type organism cultivated under the same conditions. In some embodiments the *Vibrio* sp. organism comprises a genetic modification (e.g., a deletion, mutation, inactivation, attenuation, or downregulation) in either one or both of the lpxL and lpxM genes. The *Vibrio* sp. organism of the invention therefore allows for the production and harvesting of a biological product, such as nucleic acids, biologics, proteins, single domain antibodies, antibody fragments, and other molecules of interest in the organisms with a substantially reduced or eliminated risk of sepsis in humans or animals caused by the presence of endotoxin in the products. Single domain antibodies are antibody fragments having a single monomeric variable antibody domain and can bind specifically to a particular antigen. In various embodiments their molecular weights can be 11-16 kDa or 12-15 kDa. Biological products produced by the organisms of the invention can also be peptides and peptide hormones such as angiotensin, bradykinin, bacitracin, glucagon, vasopressin are just some examples of the peptides and hormones that can be produced in the *Vibrio* sp. organisms of the invention, as well as many other nucleic acids, protein products, polypeptide, or peptide molecules.

Persons of ordinary skill in the art know that modification of genes involved in the formation of the LPS component of the outer membrane (including lpxL and lpxM) causes gram-negative organisms to become "sick" or die, or to be unculturable, or to exhibit a greatly reduced growth rate. Such modifications therefore reduce the usefulness of the organisms by making it impracticable or impossible to produce nucleic acids or polypeptides in the organisms. It was discovered by the present inventors that when the lpxL and/or lpxM genes are genetically modified in *Vibrio* sp. organisms, the organisms surprisingly remain viable and culturable, and continue to be capable of robust growth rates while producing substantially less LPS, endotoxin, or immune-stimulatory substances that are toxic to a human or other mammal compared to that produced by an unmodified or wild-type organism. The discovery is therefore valuable for methods of producing compositions containing nucleic acids, biologics and other molecules having low levels of endotoxin. Therefore, the organisms are also useful for creating products with a greatly reduced or eliminated risk of sepsis or immune response caused by endotoxin or LPS contamination in the products, or for any other use of *Vibrio* sp. The organisms modified as described herein maintain a growth rate that is substantially as robust as the unmodified organism in spite of the modification.

*Vibrio* sp.

The invention is applicable to gram negative bacteria, such as *Vibrio* sp. The organism can also be any organism of the Family Vibrionaceae. The *Vibrio* sp. organisms of the invention can be any species of the genus *Vibrio*. Some examples of organisms in the *Vibrio* genus include, but are not limited to, *Vibrio natriegens, Vibrio cholerae, Vibrio fischeri, Vibrio parahaemolyticus, Vibrio campbellii*, and *Vibrio vulnificus*, but the invention can be applied to any *Vibrio* sp. organism, or to any combination or sub-combination of the *Vibrio* sp. organisms listed herein. In one embodiment the engineered or recombinant organisms of the invention are *Vibrio natriegens*. In another embodiment the engineered or recombinant organisms of the invention are *Vibrio cholerae*. In another embodiment the engineered or recombinant organisms of the invention are *Vibrio fischeri*. In another embodiment the engineered or recombinant organisms of the invention are *Vibrio parahaemolyticus*. In another embodiment the engineered or recombinant organisms of the invention are *Vibrio vulnificus*.

Outer Membrane and Endotoxin

Lipopolysaccharide substances (LPS), also called lipoglycans or endotoxins, consist of a lipid and a polysaccharide composed of O-antigen, an outer core and an inner core joined by a covalent bond (generally depicted in FIG. 1). They are found in the outer membrane of gram-negative bacteria and elicit a strong immune response in humans and animals (i.e., are endotoxic). LPS molecules are a major constituent of the outer membrane in gram-negative bacteria. The outer membrane can have 20-25% phospholipid and about 30% LPS substances. 3-deoxy-D-manno-octulosonic acid (Kdo) is a constituent of LPS in gram-negative bacteria and connects the core polysaccharide and Lipid A (FIG. 1). The immune response is believed to be caused by the lipid portion of the complex lipopolysaccharides, which are a major component in the outer membrane of gram-negative bacteria. The Lipid A region of the LPS is believed to be anchored to the outer membrane and may be associated with the toxicity. It is also believed that the polysaccharide portion of the outer membrane may be substantially responsible for triggering the antibacterial immune response (immunogenicity) in humans and other mammals. These components that cause this toxicity and immune response are known generally as endotoxins. Any of the organisms of the invention can therefore have an outer membrane with a modified LPS versus a corresponding unmodified or wild type *Vibrio* sp. organism.

Figure 2A:
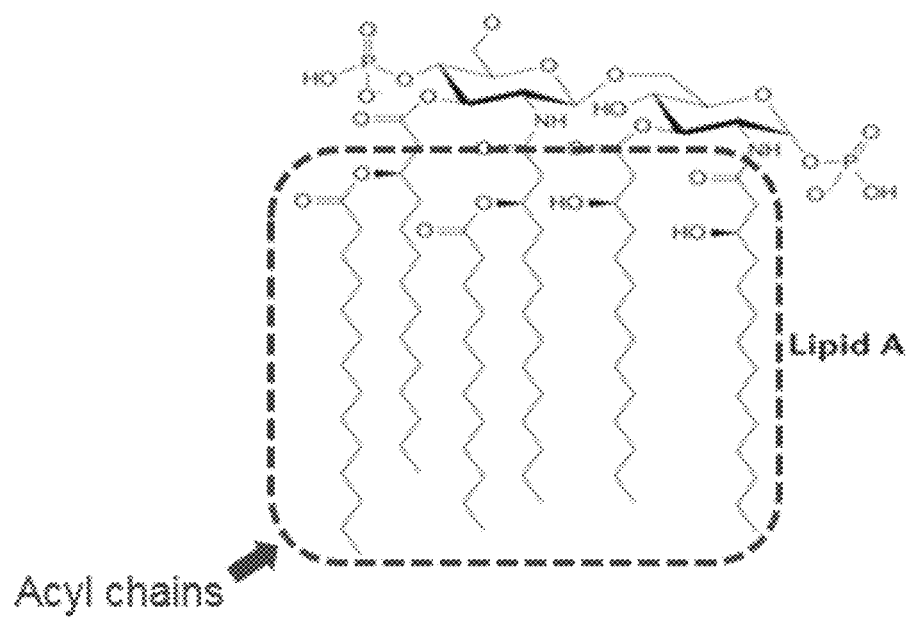
FIGS. 2A-2B, FIG. 2A provides an expanded illustration of the Lipid A component of the outer membrane of a gram negative organism, including identification of the acyl chains.
Figure 2B:
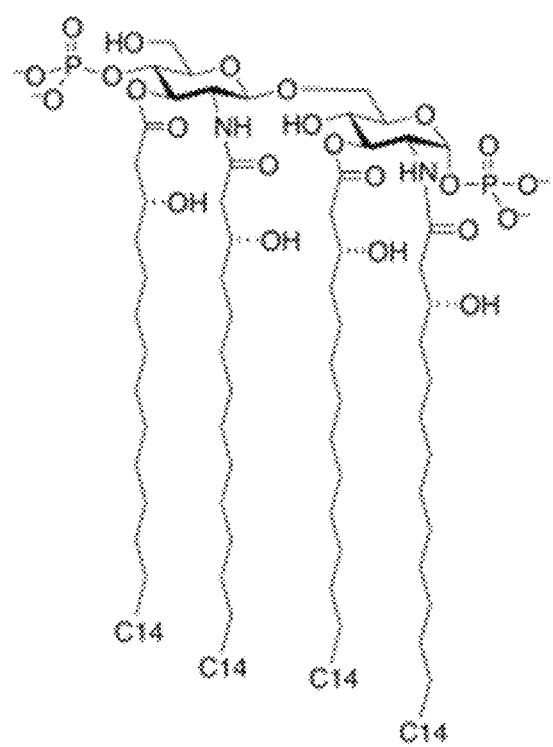

Without wanting to be bound by any particular theory it is believed that these LPS substances are present in the unmodified or wild-type organisms as the $(Kdo)_2$-Lipid A molecule, which are primarily or entirely hexaacylated (depicted generally in FIG. 2A). It is believed that by genetically modifying either one or both of the lpxL and/or lpxM genes that the Lipid A may be incompletely formed or otherwise modified to a form that may be substantially less immune stimulatory (or substantially less endotoxic) than the acylated Lipid A present in the unmodified or natural organism, and thus the recombinant organism causes a substantially lower, minimal, or no immune response (or is less endotoxic to a human, or other mammal, or bird. The recombinant organisms of the invention therefore can have a modified lipopolysaccharide component of the membrane, which in some embodiments can have a reduced number of acyl chain versus the unmodified or wild type organism. In one embodiment the acylated Lipid A in the organism of the invention can be a hexa-acylated Lipid A or a penta-acylated Lipid A. The modified lipopolysaccharides can be present in the outer membrane.

The recombinant organisms can be termed "low endotoxin," "very low endotoxin," or "endotoxin free." Therefore, products produced by methods of using these organisms (e.g., cloned nucleic acids or proteins and peptides) can avoid the lengthy and expensive endotoxin purification processes normally required, and are much safer for use in humans and animals. A low endotoxin organism (or product) is one giving an endotoxin level of 100 EU/ml or less, as determined by the endotoxin assays explained herein. A very low endotoxin organism (or product) is one giving an endotoxin level of 50 EU/ml or less, as determined by the endotoxin assays explained herein. An endotoxin free organism (or product) is one giving an endotoxin level of less than 1 EU/ml, as determined by endotoxin assays accepted in the art, for example any of those described herein.

Methods of Producing Products

The invention also provides methods of producing a biological product in a recombinant *Vibrio* sp. organism described herein. In one embodiment a biological product is a nucleic acid, which can be a DNA molecule or sequence to be amplified or cloned in the organism. In other embodiments the biological product is a protein, polypeptide, or peptide to be expressed in, and optionally secreted from, the organism. The protein, polypeptide, or peptide can be encoded by an exogenous nucleic acid in the organism. The methods involve cultivating a recombinant *Vibrio* sp. organism of the invention described herein and containing an exogenous nucleic acid to be cloned, amplified, or produced, or cultivating an organism containing an exogenous nucleic acid encoding a protein or peptide to be expressed and optionally secreted. In the methods the organism produces or contains substantially less endotoxin compared to a corresponding (wild type or unmodified) organism not having the genetic modification and cultivated under the same conditions. In the methods the recombinant *Vibrio* sp. organism can also have or exhibit a growth rate of at least 60% of the growth rate of the corresponding (wild type or unmodified) organism when cultivated under the same conditions, or have another growth rate as described herein. In the methods the recombinant organism can also produce at least 25% or at least 35% or at least 50% or at least 60% or at least 70% of the quantity of the exogenous nucleic acid to be cloned or the exogenous protein or peptide to be expressed as the corresponding organism cultivated under the same conditions and unit of time, or quantities of the nucleic acid or protein or peptide as otherwise described herein. In the methods the recombinant organism can have any of the genetic modifications described herein, and any of the characteristics of recombinant organisms described herein. Biological products produced using the recombinant cells of the invention include nucleic acids, polypeptides, peptides, and biologicals (for example any described herein), and any other molecule that can be produced in a bacterial cell.

Exogenous Nucleic Acid

The recombinant organisms of the invention can optionally comprise an exogenous nucleic acid sequence, which can be a plasmid or other vector or construct functional in the Vibrio sp. of the invention, or simply present on a plasmid, vector, or construct. Such plasmids are well known in the art. The exogenous nucleic acid can contain a sequence to be cloned or amplified, or can contain a sequence to be expressed as a heterologous protein or peptide.

As used herein, "exogenous" with respect to a nucleic acid or gene indicates that the nucleic acid or gene has been introduced (e.g., "transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. A heterologous nucleic acid can also be an exogenous synthetic sequence not found in the species into which it is introduced. Further, a nucleic acid is considered exogenous if it has been introduced into a progenitor of the cell, organism, or strain under consideration.

When applied to organisms, the terms "transgenic" "transformed" or "recombinant" or "engineered" or "genetically engineered" refer to organisms that have been manipulated by introduction of an exogenous or recombinant nucleic acid sequence into the organism, or by the manipulation of native sequences, which are therefore then recombinant (e.g., by mutation of sequences, deletions, disruptions, insertions, replacements, and other manipulations described below). In some embodiments the exogenous or recombinant nucleic acid can express a heterologous protein or peptide product. A heterologous or recombinant nucleic acid molecule can be integrated into a genetically engineered/recombinant organism's genome or, in other instances, not integrated into a recombinant/genetically engineered organism's genome, or on a vector or other nucleic acid construct. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

Recombinant or Engineered Organisms

In various embodiments the engineered or recombinant Vibrio sp. organisms of the invention comprise a genetic modification of either one or both of the lpxL and/or lpxM genes, which in one isoform have SEQ ID NOs: 1-2, respectively. A genetic modification denotes any one or more of a deletion, mutation, disruption, insertion, inactivation, attenuation, an inversion, or downregulation of a gene or other nucleic acid sequence, or any other physical change to the sequence that effects a difference in the context it occurs. An unmodified nucleic acid sequence denotes a natural or wild type sequence. The term "unmodified" can mean unmodified with respect to the gene or sequence in question, e.g., at the lpxL or lpxM genes. In various embodiments the genetic modification is a deletion or disruption of the gene.

Any genetic modification described herein can affect a demonstrable change in the organism so modified, and not be merely inconsequential to the organism's endotoxicity or growth rate. A genetic modification can decrease the organism's endotoxicity or growth rate by an amount of at least 10% or 20% or 30% or 40% or 50% or 60% or 70%. A genetic modification can also reduce the expression or activity of the modified gene by at least 10% or 25% or 40% or 50% or 70% or 90% or by 100%. And a genetic modification can increase the growth rate of the organism by at least 10% or 20% or 30% or 40% or 50% or 60% or 70%. In any of the embodiments an organism of the invention can lack one or more modification(s) that increase(s) the growth rate by any of the stated amounts. Growth rate can be measured as generation time (G), doubling time, or specific growth rate.

lpxL and lpxM genes encode fatty acid transferases involved in membrane formation. In some embodiments the recombinant or engineered organism comprises a genetic modification in either one or both of lpxL and/or lpxM gene(s). The organisms can also have (or not lack) a D-arabinose 5-phosphate isomerase (API) gene (e.g., kdsD and gutQ) and/or also have, or not lack, 2-keto-3-deoxy-D-manno-octulosonate (Kdo), any one or more of which can be natural, functional, or unmodified genes. Thus, in some embodiments the organisms of the invention can have a natural, unmodified, or wild type D-arabinose 5-phosphate isomerase (API) gene and/or a natural, unmodified, or wild type 2-keto-3-deoxy-D-manno-octulosonate (Kdo), i.e., an API or Kdo gene that has not been deleted, inactivated, disrupted, attenuated, or downregulated. In one embodiment the organism does not have a genetic modification of any gene (or any combination or sub-combination of genes) in the KDO synthesis pathway, which includes the series of enzymes that convert UDP-GlcNAc into $KDO_2$-Lipid IV(A). The organism can have wild type genes for any one of them or any combination or sub-combination of them. These enzymes include, but are not limited to, lpxD, lpxH, lpxB, lpxK, and WaaA. It can also optionally comprise a natural or unmodified transporter msbA and/or membrane protein yhjD; or in one embodiment can have only a natural, unmodified, or wild type msbA and/or yhjD gene(s) encoding a membrane protein, and have no copies of msbA or yhjD genes that are not the natural, unmodified, non-mutated, or wild type. In one embodiment the organism does not have an msbA (suppressor) mutation (e.g., has a wild type msbA gene). The recombinant organisms of the invention can also have one or more (or all) natural, unmodified, or wild type of genes involved in the synthesis and attachment of the core oligosaccharides (e.g., Waa proteins), or O-antigens (WaaL, WecA, Wzy-dependent synthesis pathways, ABC transporter-dependent pathways, and synthase-dependent pathways), and not have any non-natural or not wild type of these genes or combinations thereof.

Deletion is one type of genetic modification. A deletion can be a complete deletion or an at least partial deletion or a mutation so that the gene no longer performs its natural function and/or no longer produces a functional protein (for protein encoding genes). Thus, in some embodiments a deletion comprises a deletion of at least 10 or at least 25 or at least 50 or at least 75 or at least 100 or at least 200 or at least 300 or at least 400 or at least 500 nucleotides or at least 1000 or at least 2000 or at least 3000 or up to 5000 nucleotides. Inactivation or disruption of a gene can also be accomplished by insertion of a sequence into the gene (e.g., coding or non-coding nucleic acid sequence). A gene can also be attenuated, meaning that the gene is controlled in a manner that causes premature termination of transcription (e.g., provisional stop signaling). Downregulation of a gene is a general term meaning that the gene or nucleic acid sequence is expressed, but at a level so low that the gene or nucleic acid sequence no longer performs its natural function to a substantial degree. When a gene is a coding gene and has a modification it may no longer produce a functional protein to a substantial degree. Substantial refers to an amount that would be deemed significant to a person of ordinary skill in the context it occurs. In various embodiments a downregulated gene, or any of the genetic modifications, can be expressed at less than 50% or less than 40% or less than 30% or less than 20% or less than 10% or less than 5% or less than 1% of its expression level in a corresponding unmodified, wild type organism under similar conditions, or can be present but not expressed at all. Persons of ordinary skill with reference to this disclosure know how to perform these genetic modifications and others in a general context, and such are all considered within the scope of this disclosure. Any of these genetic modifications can also be performed in a regulatory sequence affecting expression of the gene, not necessarily in the coding region itself. The regulatory sequence can be upstream or downstream of the targeted gene. For example the deletion could be targeted to the promoter of a gene, thus preventing expression of the gene and achieving the same effect as deletion of the coding region itself. But any untranslated region associated with the gene and affecting its expression can be the target of the genetic modifications described herein. In various embodiments the *Vibrio* sp. organism of the invention does not express any lpxL gene (whether endogenous or exogenous) and/or does not express any lpxM gene (whether endogenous or exogenous).

In various embodiments *Vibrio* sp. organisms of the invention contain a deletion of either one or both of lpxL and/or lpxM, and isoforms of the genes are presented as SEQ ID Nos: 1-2. For example, in any of the embodiments the recombinant *Vibrio* sp. organisms of the invention have a genetic modification of lpxL alone, or a genetic modification if lpxM alone, or a genetic modification of both lpxL and lpxM. Any of the recombinant organisms of the invention can also have a growth rate of at least 50% or at least 55% or at least 57% or at least 60%, or at least 65% or at least 70% or at least 75% or at least 80% or at least 85% or at least 90% of the growth rate of the corresponding unmodified or wild-type *Vibrio* sp. organism under the same growth conditions, or to a *Vibrio* sp. organism that does not contain the deletion of the lpxL and/or lpxM gene(s). A corresponding organism is an organism of the same type that does not have the genetic modification being examined. A corresponding organism can be a wild-type organism, or it can be wild-type or unmodified at the gene(s) being examined. In some embodiments a corresponding organism can be the same species of organism that does not have either one or both of the lpxL and/or lpxM modifications being examined as described herein. A corresponding organism can have other modifications that do not affect the trait, gene, or genetic modification being examined.

In one embodiment the engineered *Vibrio* sp. organisms of the invention has a growth rate of at least 2× or at least 3× or at least 4× or at least 5× or at least 6× the growth rate of an *E. coli* organism having a deletion of the gutQ, kdsD, lpxL, lpxM, pagP, lpxP and eptA genes, under corresponding growth conditions. The *E. coli* organism compared can also have a mutation of the msbA148 gene to enable viability in the presence of the LPS precursor lipid IV(A).

In some embodiments the engineered or recombinant *Vibrio* sp. organisms of the invention do not comprise a genetic modification of any one or more of gutQ, kdsD, pagP, lpxP, msbA148, or any sub-combination of them. The *Vibrio* sp. organisms of the invention can therefore comprise a natural, unmodified, or wild type gutQ, kdsD, pagP, or lpxP, or all four natural or wild type genes, or any combination or sub-combination of them can be natural or wild type (i.e., natural or wild type gutQ and kdsD, or gutQ and pagP, or gutQ and lpxP, or kdsD and pagP, or kdsD and lpxP, or pagP and lpxP). Any of these organisms can also comprise an unmodified, natural, or wild type msbA148 gene with any of the combinations or sub-combinations described herein.

However, in other embodiments, the engineered or recombinant *Vibrio* sp. of the invention can comprise a genetic modification in any one of gutQ, kdsD, pagP, or lpxP, or msbA148, or any combination or sub-combination of them, as described above. In some embodiments the organisms of the invention can comprise a natural or unmodified KdsD, or Kdo8P synthase, or Kdo8P phosphatase, or CMP-Kdo synthetase, or Kdo transferase (WaaA), or any combination of these genes can be natural or unmodified.

Endotoxicity

Endotoxin refers to complex lipopolysaccharide (LPS) substances present in the outer membranes of gram negative organisms such as *E. coli, Vibrio* sp., and others. These substances are collectively called "endotoxin" and are toxic to mammals and other vertebrates. Endotoxin can be released when cells are disrupted or otherwise disintegrate. Thus, when these organisms are used to clone nucleic acids or produce proteins, polypeptides, or peptides the products can be contaminated with unacceptable levels of endotoxin. The engineered or recombinant *Vibrio* sp. organisms of the invention score substantially lower in an in vitro endotoxin assay compared to a natural, unmodified, or wild type organism under the same conditions, i.e., the recombinant organisms produce or contain substantially less endotoxin or LPS substances, or are substantially less endotoxic to humans and other mammals (e.g., canines, felines, equines, bovines, or porcines). By substantially less endotoxin or less endotoxic is meant that the organism can have less than 50% or less than 40% or less than 30% or less than 20% or less than 10% or less than 5% or less than 3% or less than 2% or less than 1% or less than 0.90% or less than 0.50% or less than 0.10% of the endotoxin content compared to a corresponding unmodified or wild type *Vibrio* sp. organism (or one that does not have the genetic modification to lpxL and/or lpxM) cultivated and measured under the same conditions. The endotoxin content or concentration, or the endotoxicity of the compared organisms can be measured using any generally accepted in vitro endotoxin assay, such as any of those described herein or otherwise accepted in the field as being a valid endotoxin assay in the context, e.g., the HEK™-Blue LPS assay, which can measure the activation of the TLR4 receptor to an endotoxin sample from an organism.

The engineered or recombinant *Vibrio* sp. organisms of the invention can also produce an endotoxin concentration of less than 50% or less than 40% or less than 30% or less than 20% or less than 10% or less than 5% or less than 1% or less than 0.50% or less than 0.10% of the endotoxin concentration produced by an unmodified or wild type *E. coli* organism (or one that does not have a genetic modification to lpxL and/or lpxM) cultivated under corresponding conditions. In some embodiments BL21(DE3) can be used as the unmodified or wild type *E. coli*. The endotoxin concentration or level can be determined using any generally accepted LPS or endotoxin assay, such as an in vitro LPS or endotoxin assay accepted in the field or described herein. Several such methods (e.g., HEK™-Blue LPS assay) are described herein.

The engineered or recombinant *Vibrio* sp. organisms of the invention can also produce an endotoxin-induced immune response of less than 50%, or less than 40%, or less than 30%, or less than 20%, or less than 10%, or less than 5%, or less than 1%, or less than 0.50%, or less than 0.10% of the response of an *E. coli* organism comprising a deletion of gutQ, kdsD, lpxL, lpxM, pagP, lpxP, and eptA, or any sub-combination of them produced under the same or corresponding conditions. The compared *E. coli* organism can also comprise a compensating mutation in the msbA gene (e.g., msbA148) (*E. coli* cells having all of the above deletions and the msbA mutation are commercially available under the trademark name ClearColi®). The endotoxin-induced immune response (or endotoxicity) can be determined or measured using an in vitro LPS or endotoxin assay. The immune response or endotoxicity can be relative to, or with respect to, the immune response in a human or other mammalian cell, and can measure activation of the TLR4 receptor. [The engineered or recombinant *Vibrio* sp. organisms of the invention can also have or produce less endotoxin (in the lower amounts stated herein and above) than the aforementioned *E. coli* organisms (e.g., the "ClearColi®" organism), which endotoxin amount can be measured using an endotoxin-induced immune response as described herein.]

The engineered or recombinant *Vibrio* sp. organisms of the invention can have an average endotoxin level for purified LPS molecules of less than 50 EU/ml, or less than 25 EU/ml, or less than 15 EU/ml, or less than 10 EU/ml, or less than 5 EU/ml, or less than 5 EU/ml, or less than 4 EU/ml, or less than 3 EU/ml, or less than 2 EU/ml, or less than 1 EU/ml, or less than 0.80 EU/ml, or less than 0.70 EU/ml, or less than 0.50 EU/ml, or less than 0.30 EU/ml, or less than 0.20 EU/ml, or less than 0.10 EU/ml, as measured in an in vitro endotoxin assay. The endotoxin level can be measured according to any generally accepted method, for example those methods described herein. Any of the organisms of the invention can also have the stated endotoxin levels disclosed herein within plus or minus 10% of the stated value. In any of the embodiments the recited values for the *Vibrio* sp. organisms of the invention can be obtained while a correspondingly prepared sample of wild type or unmodified *V. natriegens* gives a value of 107 EU/ml±5% or ±10%; or while an *E. coli* having a deletion of ΔgutQ, ΔkdsD, ΔlpxL, ΔlpxM, ΔpagP, ΔlpxP, and ΔeptA, and a mutated msbA gene (a suppressor mutation) gives a value of 146 EU/ml±5% or ±10%.

Growth Conditions

Growth conditions for the *Vibrio* sp. organisms of the invention or for wild-type *Vibrio* sp. or other gram negative organisms, for purposes of measuring growth rates comparing relative endotoxin concentrations or levels, can be any standardized or corresponding growth conditions accepted in the field as generally equivalent. In one embodiment growth rates or other activities can be calculated or conducted in LBv2 media or LB (or LB-Miller) media, at about 30° C. or another suitable temperature. The growth conditions can be utilized to compare the growth rates between gram negative or other organisms, as is known and generally accepted in the field. In any of the embodiments a suitable media (including, but not limited to, any of those described herein) having at least 10 g NaCl/L or about 1% NaCl can be used. The media can optionally contain functional amounts glucose and/or magnesium, and can contain minimal or no calcium.

Persons of ordinary skill understand that different species (or even strains) of organisms can prefer different growth conditions. Such persons understand that growing two different organisms under their different and preferred conditions for a particular measurement provides corresponding growth conditions that accurately measure or compare a parameter. Corresponding growth conditions are those accepted in the field as those suitable for providing such accurate measurements. In some embodiments the growth rate of a *Vibrio* sp. organism can be compared to an *E. coli* organism in corresponding conditions by growing *Vibrio* sp. in LBv2 media and the *E. coli* in LB (also called LB-Miller) media, since the organisms prefer these respective media. The organisms can be grown at the same temperature, e.g., about 30° C. or about 37° C., or *Vibrio* sp. can be grown at about 30° C. and *E. coli* can be grown at about 37° C. for corresponding conditions. In one embodiment *Vibrio* sp. and *E. coli* organisms can also be compared by growing both of them in LBv2 media; in another embodiment for comparison *Vibrio* sp. can be grown in LBv2 media at about 30° C. and *E. coli* can be grown in LB (or LB-Miller) media at about 37° C. for corresponding conditions. Any of these various conditions can be used to compare any properties of the organisms, whether wild type or recombinant organisms.

Growth Rate

Genetic modification (e.g., deletion, inactivation, insertion, attenuation, inversion, disruption, or downregulation) of the lpxL and/or lpxM genes in a gram negative organism would be expected to result in an organism having a significantly lower growth rate than an unmodified wild type organism. In various embodiments the organism with a significantly lower growth rate grows at 59% or less or 60% or less or 55% or less or 50% or less or 40% or less or 30% or less of the growth rate of the unmodified or wild type organism, or that (G) at least doubles, unless the organism has a modified msbA mutation (or "suppressor mutation") that permits Lipid IV(A) transport. There are various mutations of msbA that permit of increase growth and they are known to persons of ordinary skill. Yet the present inventors discovered unexpectedly that the engineered *Vibrio* sp. organisms of the invention described herein can have a genetic modification in either one or both of the lpxL and/or lpxM genes and nevertheless remain culturable and retain a high growth rate making them useful for the production of molecules as described herein. These engineered or recombinant organisms of the invention also have the advantage of giving a substantially reduced or eliminated immune response (or are substantially less endotoxic) in humans and other mammals.

A growing population of bacteria doubles at regular intervals of time. Bacterial growth occurs by geometric progression, e.g., 1, 2, 4, 8, etc. or $2^0, 2^1, 2^2, 2^3 \ldots 2^n$ where n is the number of generations. But only part of the bacterial life cycle involves exponential growth, and bacterial growth curves thus typically have an exponential portion and a stationary portion. Growth rate can be calculated during the exponential part of the life cycle. The exponential phase of growth involves balanced growth wherein the cells are dividing regularly and growing by geometric progression. The rate of exponential growth (or the growth rate) of a bacterial culture can be expressed as generation time, or doubling time of the bacterial population. Generation time (G) is defined as the time (t) per generation (n=number of generations). Thus, the equation G=time (t) divided by (n) expresses the doubling time or generation time. G can be expressed in minutes (or hours) or any suitable unit of time. For example, a generation time (G) of 10 minutes means that it will take 10 minutes for the population to double in size. In various embodiments the generation time can be measured by the numbers of organisms, the biomass, the O.D., or other measurements that are convenient and accepted as scientifically valid. Another common method of describing growth kinetics is the specific growth rate (SGR). The specific growth rate has units of reciprocal hours (per hr or $hr^{-1}$). Specific growth rate (SGR) and generation time (G) are related through the following mathematical formula: G=ln(2)/SGR. Thus, a large SGR will correspond with a small G, and vice versa. SGR can also be converted into doublings/hr by the formula: doubling time=ln(2) divided by the specific growth rate.

In some embodiments the engineered *Vibrio* sp. of the invention exhibits a specific growth rate of at least 0.30 $hr^{-1}$ (per hour) or at least 0.40 or at least 0.50 or at least 0.60 or at least 0.70 or at least 0.80 or at least 0.85 $hr^{-1}$ or 0.40-0.95 $hr^{-1}$ or 0.50-0.95 or 0.60-0.72 or 0.60-0.75 or 0.60-0.95, or 0.65-0.90, or 0.70-0.95, or 0.80-0.95, or 0.85-0.95, or 0.30-0.90, or 0.40-0.90, or 0.50-0.90, or 0.60-0.90, or 0.70-0.90, or 0.80-0.90 $hr^{-1}$ (per hour) which can be conveniently measured in any appropriate media and at any appropriate temperature (e.g., those listed herein). Thus, growth rate can be expressed in doublings/hr or in minutes/doubling or simply generation time, or specific growth rate (SGR). In one embodiment the doubling time of the organisms can be measured at 30° C. in LBv2 media. But any suitable media can be used, for example LB media (or LBMiller media). Growth can be assessed in any suitable container such as, for example, a fermentor or shake flask, but in one embodiment the organisms can be assessed in a culture or assay plate (e.g., a 48 well plate). The container can be flat bottomed microtiter plate, a round bottomed microtiter plate, or another appropriate vessel with wells of advantageous shape, for example flower shaped wells (e.g., FlowerPlate® microtiter plates). Any suitable container and conditions can be used to measure the growth rate. The growth rate or specific growth rate can also be assessed at various temperatures, including but not limited to, growth at about 25° C. or about 30° C. or at about 37° C. or at about 40° C. or at about 42° C. or about 25-30° C. or 25-32° C. or 25-37° C. or about 30-37° C. or about 37-42° C. or at any temperature between 16-42° C. The growth rates disclosed herein are achievable on the media indicated herein and without any further supplementation of the media (e.g., without supplementation by arabinose 5-phosphate or glucose 6 phosphate). In some embodiments the organisms can have all wild type genes and no deletions or genetic mutations to any gene except as otherwise described herein.

In various embodiments the engineered or recombinant organisms of the invention have a doubling time of about 60 minutes, or 55-70 minutes, or 40-50 minutes, or 30-40 minutes, or less than 30 minutes at 30° C., or less than 22 minutes at 37° C., or less than 21 minutes at 42° C., all in LB or LBv2 media.

The engineered or recombinant *Vibrio* sp. organisms of the invention can grow more slowly than a corresponding or wild type organism (or one not having the genetic modification to lpxL and/or lpxM). Thus, in various embodiments the engineered or recombinant *Vibrio* sp. organisms of the invention can have a growth rate of at least 40% or at least 50%, or at least 55%, or at least 60% at least 65% or at least 70% or at least 80% or at least 85% or at least 90% or 50-70% or 55-70% or 55-65% or 55-80% or 55-90% or 60-70% or 60-65% or 60-80% or 60-90% or 60-95% or 65-90% or 70-90% or 75-90% or 55-95% or 65-95% or 70-90% or 70-95% or 75-95% of the growth rate (but also optionally less than 100% or less than 95% or less than 90% for any of them) of the corresponding or wild-type organisms (or those not having the lpxL and/or lpxM modification(s)) under the same or corresponding conditions. For example, if any organism has a doubling time of 10 minutes, 65% of its growth rate can be calculated as 10/0.65=15.4 minute doubling time. Growth rates can be measured over any convenient time period of cultivation during the exponential phase, such as over 4 hours or over 6 hours or 8 hours or 9 hours or 10 hours or 12 hours or 15 hours or 18 hours or 24 hours or only from 0-3 hours or 0-4 hours or 0-6 hours or 0-8 hours or 6-8 hours or from 8-10 hours or from 8-12 hours or from 10-12 hours. Thus, the recombinant *Vibrio* sp. organisms of the invention can have a doubling time or generation time or specific growth rate of 50% or greater or 55% or greater or 60% or greater, or 65% or greater, or 70% or greater or 75% or greater or 80% or greater or 85% or greater or 90% or greater, or 95% or greater (or 55-70% or 55-65% or 55-90% or 55-95% or 60-70% or 60-65% or 60-80% or 60-90% or 60-95% or 65-90% or 65-95% or 70-90% or 75-90% or 80-90% or 75-95% or 80-95%) than the doubling time or generation time of the wild-type organism, or an organism not having the genetic modification of lpxL and/or lpxM. Doubling time can be expressed as any suitable unit of time, but doublings/hr is convenient and commonly used.

Any of the recombinant *Vibrio* sp. organisms described herein can also have a growth rate of at least 2× greater, or at least 3× greater or at least 4× greater or at least 5× greater or at least 6× greater or at least 7× greater or at least 8× greater or at least 10× greater than an *E. coli* having a deletion of ΔgutQ, ΔkdsD, ΔlpxL, ΔlpxM, ΔpagP, ΔlpxP, and ΔeptA, and a mutated msbA gene (a suppressor mutation). Such *E. coli* are commercially available under the trademark name ClearColi®).

Any of the engineered or recombinant *Vibrio* sp. organisms of the invention can exhibit sustained growth at higher temperatures, for example at about 40° C., or above 40° C., or at about 42° C., or above 42° C., or at about 37-42° C. or about 38-42° C., e.g., for time periods of at least 12 hours or at least 18 hours or at least 24 hours or at least 48 hours. In some embodiments the cells can be re-cultured after being exposed to the stated conditions.

Endotoxin Assay

Various methods are available for measuring the level of endotoxin in a sample or for comparing the levels of endotoxin in samples. In one embodiment the HEK™-Blue LPS assay is used, but any in vitro endotoxin or LPS assay that is generally accepted or that has been scientifically demonstrated as reliable and is based on LPS-induced activation of a mammalian TLR4 receptor can be used. In some embodiments the endotoxin or LPS assay is a cell-based and/or colorimetric assay, like the HEK™-Blue LPS assay. Endotoxin or LPS levels can be measured in samples of cells or in a sample of a product of cells.

The HEK-Blue™ LPS assay is a cell-based colorimetric assay for detecting endotoxin. It is based on the ability of the TLR4 receptor to recognize and be activated by LPS from gram-negative bacteria. The assay utilizes HEKBlue™-4 cells, which are highly sensitive to LPS and, in particular, to the toxic Lipid A moiety of LPS found in wild type gram negative organisms such as Vibrio sp. and E. coli. The cells used in the HEK-Blue™ LPS assay are engineered to stably express human TLR4 and an NF-kB-inducible secreted embryonic alkaline phosphatase reporter gene. In some embodiments the HEK-Blue™ LPS assay is utilized to measure or compare endotoxin activation of the TLR4 receptor in respective samples, e.g., unmodified or wild type samples versus the recombinant Vibrio sp. organisms of the invention, or other organisms. In various embodiments the TLR4 receptor can be a human TLR4 receptor, but animal receptors can be used for animal products. For example, a canine, feline, equine, porcine, TLR4 receptor can optionally be used when evaluating products for animals.

Monocyte activation tests (MATs) are another example of suitable and reliable endotoxin or LPS detection assays that can be used in the present invention. Monocytes contain cell-surface receptors for LPS molecules and LPS elicits a strong response from monocytes when it binds to toll-like receptor (TLR4) on the cell surface. MAT assays are in vitro assays based on this binding, which sets off a cascade of reactions resulting in the release of cytokines. These assays can be based on human whole blood. Other endotoxin tests also based on TLR4 activation can also be used in the invention.

The level of endotoxin or LPS in a sample can be expressed as endotoxin units per ml (EU/ml). In various embodiments the endotoxin or LPS assay selected can reliably measure endotoxin concentrations of about 0.1 EU/ml or less, or about 0.05 EU/ml or less, or about 0.03 EU/ml or less, or about 0.02 EU/ml or less, or about 0.01 EU/ml or less than 100 ng/ml or less than 10 ng/ml or less than 1 ng/ml or less than 0.5 ng/ml or less than 0.4 ng/ml or less than 0.3 ng/ml or less than 0.2 ng/ml or less than 0.1 ng/ml. In various embodiments other methods of measuring endotoxin level can also be used such as, for example, gel clot assays, or turbidimetric assays, or chromogenic assays, or any generally accepted method. The Examples provided herein also illustrate methods of calculating the endotoxin level of an organism or sample.

The HEK-Blue™ assay and other accepted endotoxin assays can give an endotoxin measurement in a unit of concentration, for example ug/ml or ng/ml. However, endotoxin samples can also have differing potencies. To address this the FDA established a standard endotoxin preparation expressed in units of activity instead of mass using a universal standard called the reference standard endotoxin (RSE). According to the current FDA standard, the RSE equates to 10 EU/ng (EC-6 RSE). Thus, mass units or units of concentration can be easily converted into EU/unit volume or EU. Control standard endotoxin (CSE) are also commonly provided in commercially available kits for measuring endotoxin and are secondary standards, i.e., are standardized against the RSE. CSEs are also generally accepted and widely used in the field and are useful for building standard curves for quantitation.

LPS extraction and purification methods are well known and kits are commercially available. The LPS extraction and purification methods are known in the art and are scientifically accepted, and are part of the LPS assays discussed herein for determining endotoxin levels of samples or organisms. In any of the embodiments described herein the LPS extraction method can be performed on a culture volume of 5 ml at an OD600 of 0.8-1.2 for evaluation or determination of any of the endotoxin values described herein. If desired, dilutions can be performed until a wild type or unmodified V. natriegens gives a value of 107±5% or ±10%; or until an E. coli having a deletion of ΔgutQ, ΔkdsD, ΔlpxL, ΔlpxM, ΔpagP, ΔlpxP, and ΔeptA, and a mutated msbA gene (suppressor mutation) gives a value of 146±5% or ±10%.

The invention also provides kits comprising a recombinant Vibrio sp. organism described herein, which can optionally contain a vector for cloning a nucleic acid sequence or for expressing a protein or peptide. In some embodiments the kits can also contain growth media for growing the organisms, a recovery media or buffer for growing cells after transformation and/or a positive control vector, to verify that the transformation protocol was correctly followed. The growth media, recovery media, and buffer for growing cells after transformation can be any described herein.

EXAMPLES

Example 1

Construction of Vibrio Strains with ΔlpxL, ΔlpxM, ΔeptA

This example demonstrates the preparation of a recombinant Vibrio natriegens organism of the invention, in this embodiment having deletions of ΔlpxL and ΔlpxM. Various methods for deleting or otherwise inactivating these genes are known to those skilled in the art.

Figure 5:
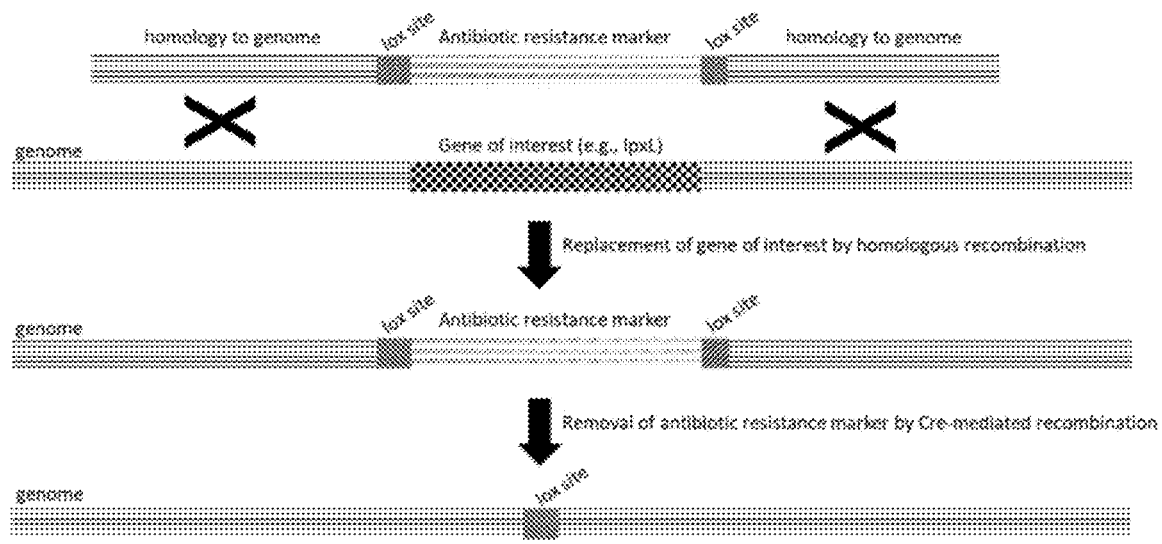
FIG. 5 is an illustration of an overview of genome engineering via natural transformation.

Vibrio natriegens strains were transformed with plasmid p15a-Vc-tfoX using established electroporation or chemical transformation protocols. p15a-Vc-tfox is a plasmid containing the p15a origin of replication, a gene encoding the beta-lactamase protein (to confer antibiotic resistance to ampicillin and carbenicillin), and contains a copy of the V. cholerae tfoX gene under the control of the IPTG-inducible tac promoter. This allows inducible activation of the competence machinery and enables strain engineering via natural transformation. Briefly, cells of V. natriegens rendered naturally competent using known protocols were transformed with linear DNA constructs designed to delete the target genes (e.g., lpxL). In one embodiment (generally depicted in FIG. 5) the construct contained an antibiotic resistance marker bounded by lox sites, flanked on either side by 3 kb of DNA homologous to the regions of the genome that are immediately upstream and downstream of the gene of interest. This construct integrates into the genome by homologous recombination, displacing the gene of interest. The antibiotic selection marker was used to distinguish transformed vs untransformed cells. Proper integration of the deletion cassette was determined by known methods such as diagnostic PCR. The antibiotic resistance marker can be removed via Cre-mediated recombination between the lox sites.

In another embodiment, deletion of these genes is performed with allelic exchange plasmids. Briefly, allelic exchange plasmids are constructed containing an origin of replication that does not replicate in V. natriegens (R6K), an origin of transfer (oriT) (from plasmid RP4 (a.k.a. RK2)) to enable plasmid transfer by bacterial conjugation, a negative selection marker (ccdB), and a selectable marker (chloramphenicol acyltransferase) flanked on either side by DNA (0.5-3 kb in length) that is homologous to V. natriegens genomic DNA that is upstream and downstream of the gene targeted for deletion. The allelic exchange plasmids can have the sequences of SEQ ID NO: 3-4. The plasmids are introduced into a conjugation-proficient E. coli strain (e.g., 517-1λ pir), which can then be mobilized by conjugation into the *V. natriegens* strain. Following conjugation, cells are plated on media that only supports the growth of *V. natriegens* (to kill the *E. coli* conjugation strain) and that contains appropriate antibiotics to select for *V. natriegens* cells that took up the plasmid by conjugation. Since the plasmid is incapable of replication in *V. natriegens*, the only way *V. natriegens* cells can survive the selection is if the plasmid has integrated into the genome. The means of integration may be homologous recombination between the genome and the homologous flanking sequences on the plasmid. Double-crossover events (where the gene of interest is replaced by the selectable marker) can be identified by leveraging the negative selection cassette (ccdB) to negatively select for cells that have lost the plasmid backbone, but retain the selectable marker. The selectable marker is excised by Cre-mediated recombination, when lox recognition sites are present on either side of the marker.

Example 2

Measuring Immunogenicity of Purified Endotoxin Molecules

Various strains of *V. natriegens* and *E. coli* were selected to analyze the immunogenicity of their purified LPS molecules. For *E. coli*, we selected the commonly used TransforMax™ EPI300™ strain (Epicentre®), and a commercially available *E. coli* strain containing several gene knockouts (including ΔgutQ, ΔkdsD, ΔlpxL, ΔlpxM, ΔpagP, ΔlpxP, and ΔeptA, and a mutation in msbA) as a low endotoxin alternative (commercially available as ClearColi® BL21(DE3) from Lucigen®). For *V. natriegens* we selected a strain derived from the type strain of the species with ΔlpxL and ΔlpxM deletions (*V. natriegens* ΔlpxL, ΔlpxM) and an unmodified type strain without the deletions (*V. natriegens* wt). The type strain is defined in the International Code of Nomenclature of Bacteria and is known as the reference strain for the species, and against which subsequent strains will be compared.

LPS was purified from these strains as follows. *E. coli* strains were grown overnight at 37° C. with agitation at 200 rpm in LB-Miller media (5 g/L yeast extract, 10 g/L tryptone, 10 g/L NaCl). *V. natriegens* strains were grown overnight at 30° C. with agitation at 200 RPM in LBv2 media (LB-Miller media (5 g/L yeast extract, 10 g/L tryptone, 10 g/L NaCl) supplemented with additional 204 mM NaCl, 4.2 mM KCl, and 23.14 mM $MgCl_2$). On the following day, 1-5 ml of overnight culture was pelleted for 2 min at 17,000×g at room temperature. The supernatant was then completely removed, leaving only the wet bacterial pellet. 25 mg of each bacterial pellet was used for LPS extraction, which was performed using a commercially available LPS extraction kit according to the manufacturer's protocol (including an optional proteinase K digestion step). Samples were stored at −20° C. until further use.

Endotoxin-induced immunogenicity was measured using the HEK-Blue™ LPS Detection Kit (InvivoGen®) according to the manufacturer's protocol. With this kit, the presence of immune-stimulatory forms of LPS in the cell culture results in a detectable absorbance at 620-655 nm that is proportional to the amount of endotoxin present. The kit included endotoxin standard (CSE) that was used as a positive control and endotoxin-free water was used as a negative control. A standard curve was prepared from the endotoxin standard from a series of 1:2 serial dilutions (performed in duplicate and replicated on each assay plate).

Figure 6:
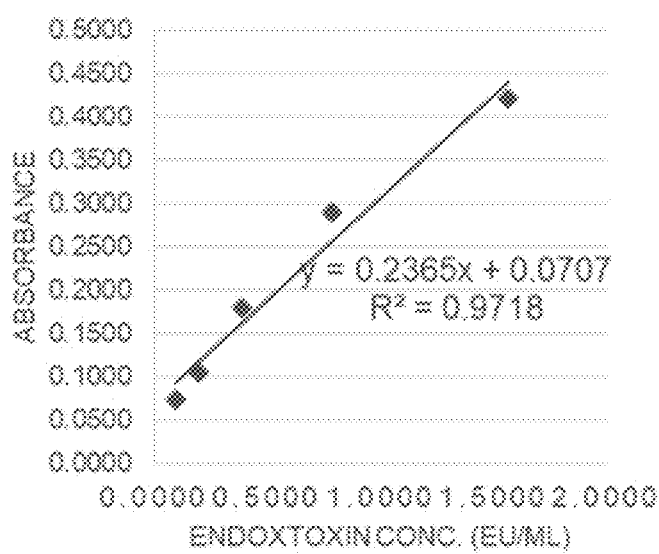
FIG. 6 provides a graph showing an example standard curve for the endotoxin assay conducted in Example 2. A linear curve is displayed.

A series of 1:3 serial dilutions of purified LPS samples from the *E. coli* and *V. natriegens* strains were measured in duplicate. A standard curve of endotoxin concentration (EU/mL) vs. absorbance (655 nm) was plotted for the reference LPS material. A line was fit to the linear portion of the standard curve and was used to calculate the immune response of the purified LPS samples. Where the response for our samples is below or above the linear range of the standard curve, the values are presented as the highest or lowest possible values, respectively, based on the range of the standard curve. An example standard curve is shown in FIG. 6, and a linear standard curve was obtained. The endotoxin quantitation results are shown below:

TABLE 1

| Results of Sample v. Average Endotoxin Assay (EU/ml) | |
| --- | --- |
| wt *E. coli* | >15,000 |
| ClearColi ® | 146 |
| *V. natriegens* wt recombinant *V. natriegens* | 107 |
| ΔlpxL, ΔlpxM | <0.097 |

As shown in Table 1, the recombinant *V. natriegens* of the invention gave an endotoxin assay result of only 0.097, i.e., free of endotoxin. This level was less than 1% of the unmodified (or wild type) *V. natriegens*, and less than 1% of the endotoxin reading from the commercially available, "low endotoxin" *E. coli* known as ClearColi®. It was also less than 1% of unmodified or wild type *E. coli*.

Example 3

Measuring Growth Rate of Engineered and WT Strains of *E. coli* and *V. natriegens*

The growth rates of a wt *E. coli* strain (BL21(DE3)), an LPS-engineered *E. coli* strain (ClearColi® BL21(DE3) from Lucigen®), an unmodified wt *V. natriegens* strain, and a recombinant (LPS engineered) *V. natriegens* strain of the invention (ΔlpxL, ΔlpxM) were determined as follows. *V. natriegens* strains were grown in LBv2 media (LB-Miller media (5 g/L yeast extract, 10 g/L tryptone, 10 g/L NaCl) supplemented with additional 204 mM NaCl, 4.2 mM KCl, and 23.14 mM $MgCl_2$), while *E. coli* strains were either grown in the recommended LB-Miller media (5 g/L yeast extract, 10 g/L tryptone, 10 g/L NaCl) or LBv2 (for comparison to *Vibrio*). Cultures grown overnight in flasks with agitation at 200 rpm to stationary phase at either 37° C. (for *E. coli*) or 30° C. (for *V natriegens*) were re-cultured in fresh media to an OD600 of 0.1-0.3. These actively growing cultures were diluted again to an OD600 of 0.01 in their respective media, and 800 uL of each culture was added to wells of either FlowerPlate® (flower-shaped wells) or Round Well plate 48-well microtiter plates designed for use with a BioLector® I benchtop microfermentation system (m2p-Labs™). The different well geometries can give rise to different growth rates, believed due to differences in sheer stress, agitation, and the rate of oxygen transfer. The cultures were grown at 30° C. at 1200 rpm with 85% humidity. Measurements of biomass (scattered light intensity), $pO_2$, and pH were recorded for all cultures at 10-minute intervals for a 12 hr period.

To determine specific growth rate, the natural logarithm was taken of all biomass measurement time points, and the slope of the linear portion from the transformation to natural log was determined. Values were calculated using the average of 5 or 6 biological replicates for the round bottom and FlowerPlates®, respectively. The error bars represent the standard deviation. The absolute growth rates are highly dependent upon the format of the experiment (e.g., growth in a microtiter plate vs. a baffled flask vs. a fermenter), but the experiment described above is useful for determining relative differences in growth rate between different strains. The growth rates are presented in FIG. 3A and in tabular form in Table 2 below:

TABLE 2

Growth Data in Tabular Format

| Strain | Media | Growth Rate (hr-1) | |
|---|---|---|---|
| | | FlowerPlate ™ | Round Bottom Well |
| E. coli BL21(DE3) | LB media | 0.193 | 0.597 |
| | LBv2 media | 0.471 | 0.434 |
| E. coli ClearColi ® BL21(DE3) | LB media | 0.106 | 0.16 |
| | LBv2 media | 0.089 | 0.149 |
| V. natriegens (wt) | LBv2 media | 0.758 | 0.903 |
| V. natriegens (ΔlpxL, ΔlpxM) | LBv2 media | 0.645 | 0.698 |

Figure 3A:
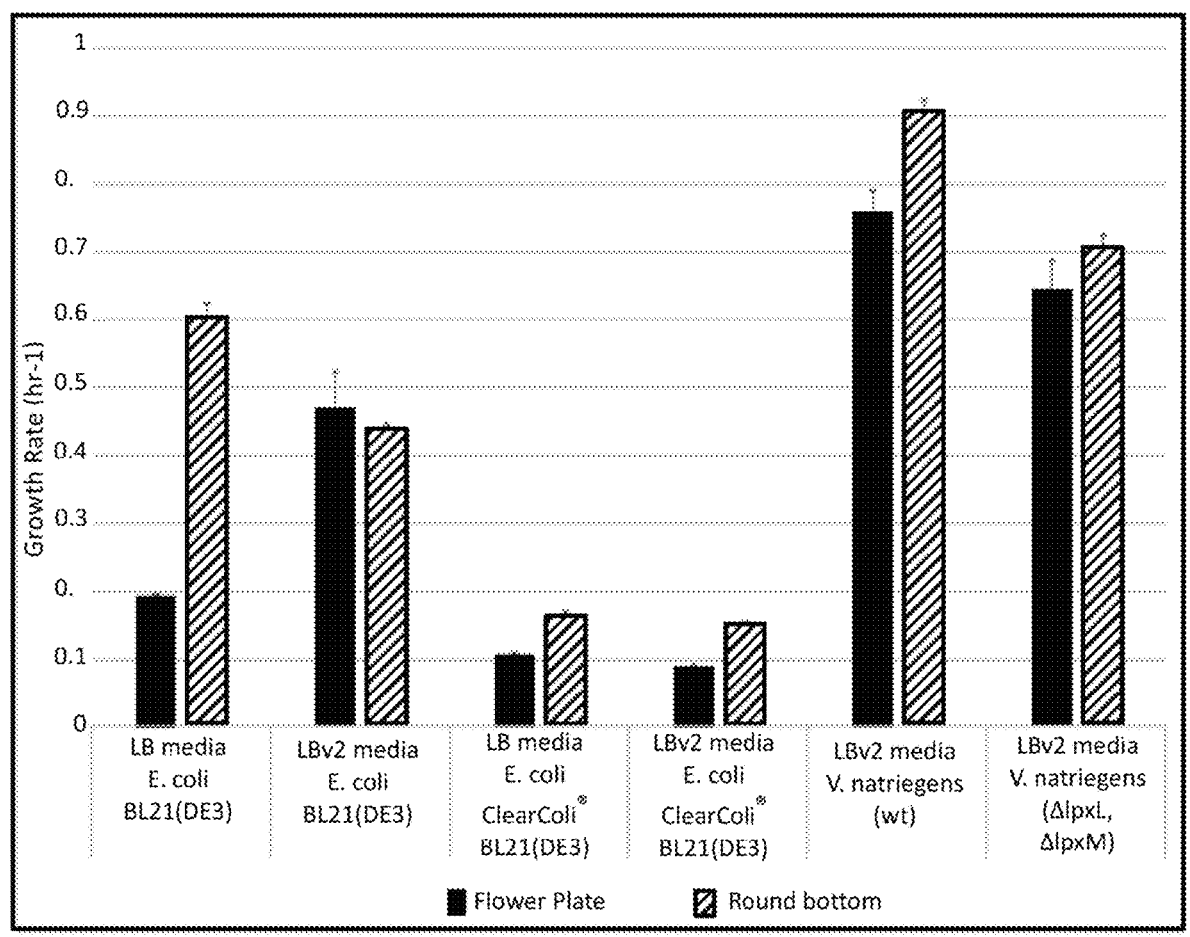
FIG. 3A-3B, FIG. 3A provides a bar graph illustrating the difference in specific growth rates of a wild type *E. coli* (BL21(DE3)), an endotoxin-reduced *E. coli* (commercially available ClearColi®), a wild type *Vibrio natriegens*, and a recombinant *Vibrio natriegens* of the invention, having a deletion of lpxL and lpxM.
Figures 3B, 4:
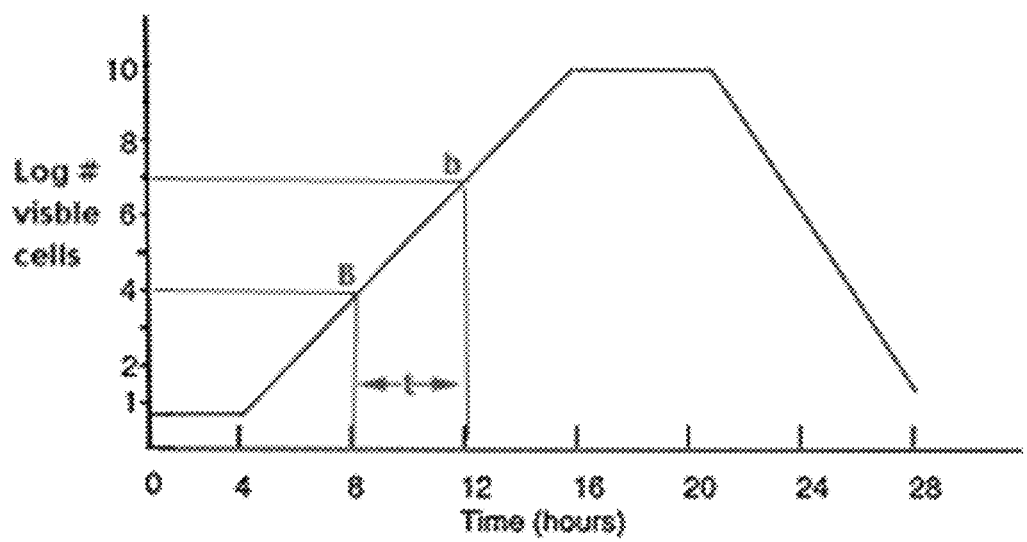
FIG. 4 is an example of calculating the growth rate of a bacterial sample and shows the exponential growth portion of the bacterial life cycle (in logarithmic format), from which readings are taken.

As illustrated in FIG. 3A and Table 2, the recombinant *V. natriegens* of the invention exhibited a growth rate of about 85% that of the unmodified *V. natriegens* organism in a FlowerPlate™ microtiter plate, and about 77.3% in a round bottom well.

The recombinant *V. natriegens* also exhibited a growth rate of more than 7× that of low endotoxin *E. coli* grown in the same media (LB(Miller) and LBv2 media) in a FlowerPlate™ microtiter plate, and more than 6× low endotoxin *E. coli* grown in LB media. The recombinant *V. natriegens* also exhibited a growth rate of more than 4.6× that of low endotoxin *E. coli* grown in the same media (LBv2 media) in a round bottom microtiter plate, and more than 4.3× low endotoxin *E. coli* grown in LB media.

Example 4

Preparation of Plasmid DNA and Single Gene Knockouts

This example shows application of the invention in an application where endotoxin contamination is of concern, which is the preparation of plasmid DNA for therapeutic or research use. This example also shows that a genetic modification or deletion to either lpxL or lpxM provides the low endotoxin benefit.

Figure 8:
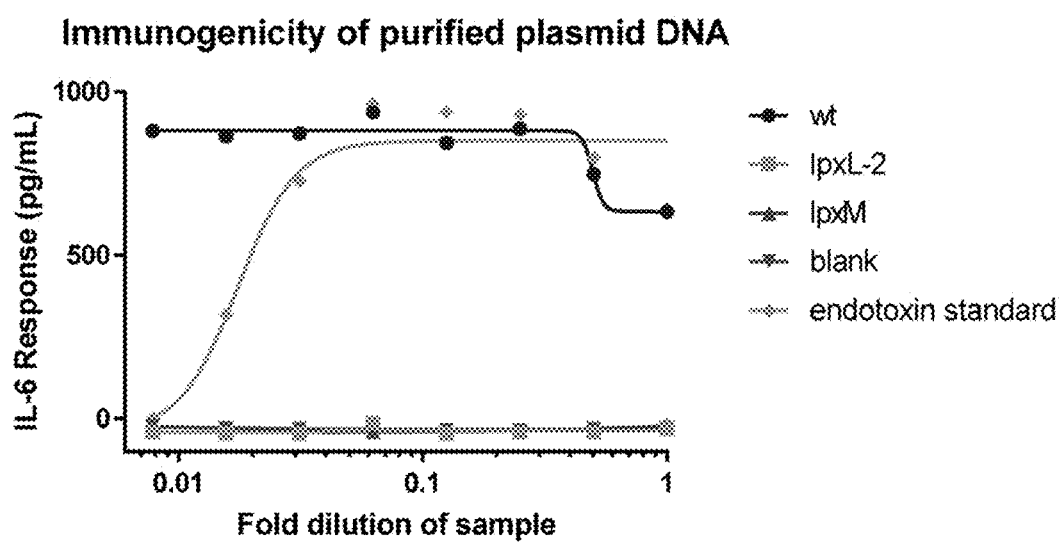
FIG. 8 is a graphical illustration showing the immunogenicity of *Vibrio* organisms having ΔlpxM and ΔlpxL deletions versus wild type organisms.

FIG. 8 shows the immunogenicity of plasmid DNA samples purified from various *V. natriegens* strains. Eight 1:2 serial dilutions were prepared and examined for each sample in order to measure the response across a wide range of sample concentrations. Briefly, purified plasmid preparations were prepared from bacterial cultures using QIAprep® Spin Miniprep kits (following the manufacturer's protocol) and eluted in 50 uL of the kit elution buffer. Immunogenicity of sample preps was analyzed via Monocyte Activation Test. In this test, human PBMCs isolated from human whole blood are cultured in the presence of the samples, and immunogenicity is determined by measuring the production of IL-6, a proinflammatory cytokine. IL-6 levels are determined via ELISA.

FIG. 8 shows the unmodified *V. natriegens* induces a strong IL-6 response across the entire dilution series. On the other hand, strains with a deletion of either lpxM or lpxL show responses that are indistinguishable from the buffer blank (negative control), demonstrating that these samples do not induce an immune response even with an undiluted plasmid preparation. A dilution series of *E. coli* LPS is included as an endotoxin standard (top concentration is 5 EU/mL, additional samples represent a 1:2 serial dilution series).

Example 5

Generation Time

This example provides an example of how to calculate the generation time of a bacterial population. We assume the following growth data was recorded for a bacterial population. Biomass denotes an arbitrary measurement of the amount of cells in a population, in various examples it can correspond to dry weight of cellular material, the number of cells, or the measurement of the optical density of the culture (e.g., at 600 nm), etc.).

TABLE 3

| Time (hrs) | Biomass |
|---|---|
| 0.5 | 4 |
| 1 | 16 |
| 1.5 | 64 |
| 2 | 256 |
| 2.5 | 1,024 |
| 3 | 4,096 |
| 3.5 | 8,192 |
| 4 | 12,288 |
| 4.5 | 13,517 |
| 5 | 13,600 |

Figure 7A:
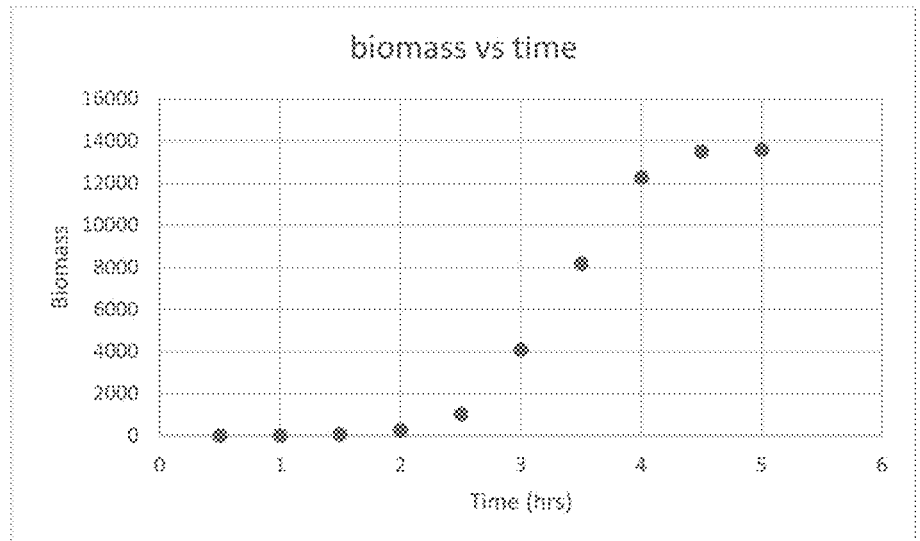
FIG. 7A-7C, FIG. 7A is a graphical illustration of a biomass v. time curve showing exponential growth.
Figure 7B:
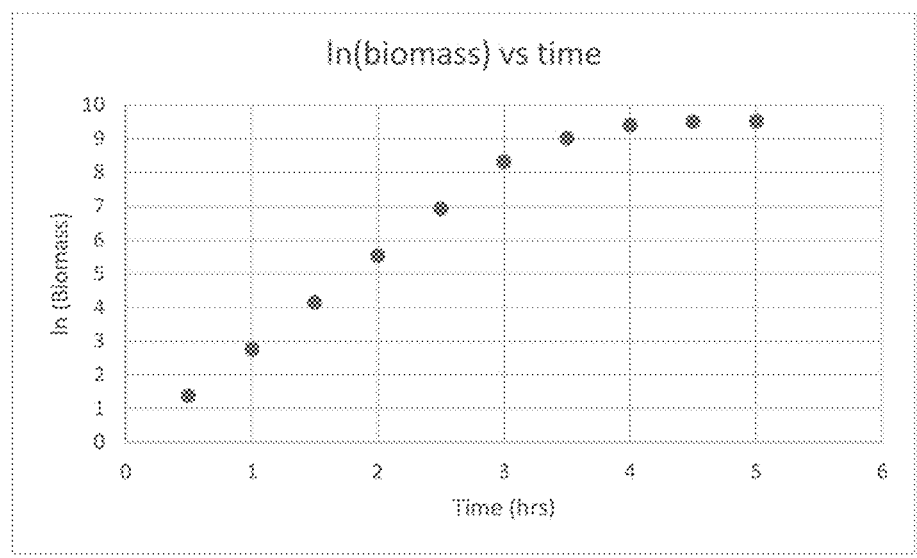
Figure 7C:
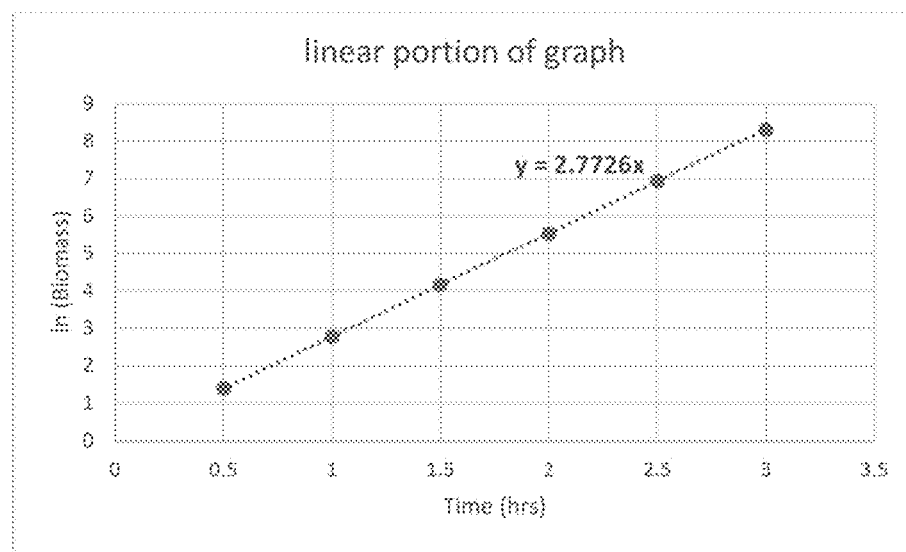

These data are plotted, giving the graph illustrated in FIG. 7A. A natural log transformation of the biomass measurements is performed and gives rise to the semi-log graph of FIG. 7B. The linear portion of the graph is identified, and a line is fit to the data, as shown in FIG. 7C. The resulting line has the formula y=2.7726x, where 2.7726 is the slope of the line. This value (2.7726) corresponds to the specific growth rate, and has units of $(hr^{-1})$ (per hour). The specific growth rate can be converted to doubling time (hours/doubling) by using the following mathematical relationship:

$$G=\ln(2)/SGR$$

where G corresponds to the doubling time, and SGR corresponds to the specific growth rate. Performing this calculation with the data:

$$G=\ln(2)/2.7726=0.249999 \text{ hours/doubling.}$$

Although the invention has been described with reference to the above examples, it will be understood that modifications and variations are encompassed within the spirit and scope of the invention. Accordingly, the invention is limited only by the following claims.

What is claimed is:

1. A method of cloning a nucleic acid or of producing a protein comprising:
    culturing a recombinant *Vibrio* sp. organism comprising:
        an exogenous nucleic acid sequence for cloning by the organism, or an exogenous nucleic acid sequence encoding a heterologous protein or peptide for production by the organism;
        a genetic modification selected from deletion, inactivation, or disruption of the lpxL gene or the lpxM gene, wherein the organism produces substantially less endotoxin compared to a corresponding organism not comprising the deletion, inactivation, or disruption and cultivated under the same conditions; and
        wherein the recombinant *Vibrio* sp. organism exhibits a growth rate of at least 60% of the growth rate of the corresponding organism when cultivated under the same conditions;
    wherein the organism has an endotoxin level of less than 50 EU/ml of purified lipopolysaccharide; and
    harvesting the nucleic acid sequence cloned by the organism, or the protein or peptide produced by the organism.

2. The method of claim 1, wherein the organism does not express an exogenous or endogenous lpxL or lpxM gene.

3. The method of claim 1, wherein the organism does not comprise a deletion, inactivation, or disruption in any gene selected from the group consisting of: gutQ, kdsD, pagP, and lpxP.

4. The method of claim 1, wherein the recombinant organism exhibits a growth rate of at least 70% of the growth rate of a corresponding unmodified *Vibrio* sp. organism under identical conditions.

5. The method of claim 1, wherein the recombinant organism has an average endotoxin level of less than 1 EU/ml measured in an in vitro assay.

6. The method of claim 1, wherein the recombinant organism has a doubling time of 55-70 minutes at 30° C.

7. The method of claim 1, wherein the growth rate is measured over a period of 8 hours.

8. The method of claim 1, wherein the growth rate is measured over a period of 12 hours.

9. The method of claim 1, wherein the genetic modification is a deletion.

10. The method of claim 1, wherein the recombinant organism is *Vibrio natriegens*.

11. The method of claim 1, wherein the organism has an endotoxin level of less than 1 EU/ml, and a specific growth rate of 0.60 to 0.72 at 30° C. in LBv2 media.

12. The method of claim 1, wherein the recombinant *Vibrio* sp. organism produces at least 25% of the quantity of the exogenous nucleic acid for cloning or at least 25% of the exogenous protein for expression under the same conditions as the corresponding organism when cultivated under the same conditions.

13. The method of claim 1, wherein the quantity of exogenous nucleic acid for cloning or the protein expression is measured over a period of 12 hours.

14. The method of claim 13, wherein the exogenous nucleic acid encodes a protein that is produced by the organism.

15. The method of claim 14, wherein the protein produced is secreted from the cell.

16. The method of claim 1, wherein the recombinant *Vibrio* sp. organism has an endotoxin level of less than 10 EU/ml measured in an in vitro assay.

17. The method of claim 16, wherein the recombinant *Vibrio* sp. organism exhibits a growth rate of at least 80% of the growth rate of the corresponding organism when cultivated under the same conditions.

18. The method of claim 17, wherein the recombinant *Vibrio* sp. organism has an endotoxin level of less than 1 EU/ml measured in an in vitro assay.

* * * * *

SEQUENCE LISTING

<160> NUMBER OF SEQ ID NOS: 4

<210> SEQ ID NO 1
<211> LENGTH: 975
<212> TYPE: DNA
<213> ORGANISM: Vibrio natriegens
<220> FEATURE:
<223> OTHER INFORMATION: lpxL

<400> SEQUENCE: 1

| | | | | | |
|---|---|---|---|---|---|
| atgggcacat | ctggcgattc | tttcatgaac | aaacaaaaag | agcctgtttt | cgaggctcgg | 60 |
| ttcctaatgc | ctcggtactg | gggaactcta | ctcatcatcg | gggtgatgta | tttacttagc | 120 |
| cttctacctt | tcaaatttca | attattcctg | ggacgcagta | ttggccgttt | ggccatgcga | 180 |
| ttaatgaaaa | agcgtcaggt | caccattcgt | cgcaatttag | agctctgctt | cccgaagatg | 240 |
| gacgagagca | aacgagaagc | gatactgaaa | gctaacatcg | ataattctgg | cattgcactg | 300 |
| tttgagacag | cgatggcttg | gttctggccg | gatcgcaggg | ttaataaaca | cgtaacgata | 360 |
| aaagggatgg | aacacctaga | agcgttagaa | aaagacggca | aggggtgtt | gatgcttgcc | 420 |
| gttcattcca | tgaacttaga | gctgggtgca | cgtgcatttg | gcattcaaaa | atctggaatg | 480 |
| ggtgtttatc | gaccgaataa | caatccttgt | tttgactatt | ttcagtacaa | gggtcgttcg | 540 |
| cgttccaatc | gtactttgat | cgatcgtaaa | aatgttagag | gaatgctgga | cgcttttgaat | 600 |
| tccggcaatc | gcgtttggta | tgcgcctgac | catgattatg | gaaccagaag | atcgaccttt | 660 |
| gcgcctttgt | ttgctgtcaa | aaacgcctgt | accacaacag | gcaccagttt | acttgttgat | 720 |
| gcaacagatt | gtgcgattgt | gccgtttacc | atggtaagag | gggatgatgg | ccattacaca | 780 |
| ttaacgatca | gggagccagt | tgacggattt | cctaaaggtg | ataccagaaa | cgcggcgatt | 840 |
| tttatcaata | aaattgttga | agagtcgatt | atggctagcc | ctagtcaata | catgtggttg | 900 |
| caccgccgat | ttaaaaccag | accgcaaggt | gaagattgtt | tgtacaatcc | tcagttaatc | 960 |
| cctgcgatga | gttag | | | | | 975 |

<210> SEQ ID NO 2
<211> LENGTH: 981
<212> TYPE: DNA
<213> ORGANISM: Vibrio natriegens
<220> FEATURE:
<223> OTHER INFORMATION: lpxM

<400> SEQUENCE: 2

| | | | | | |
|---|---|---|---|---|---|
| atgatcaata | aacgtgatga | tttcgatccc | aaagcctata | accctgagtt | tgaccgctca | 60 |
| tttctcaagc | ctaaatattg | gggaacctgg | ctcgctgttt | ttagctcaat | ttttatcgca | 120 |
| ttgctgcccc | tcgcttttca | ccagtggctg | gcaaaagtgc | tggcatcacg | tttagttaaa | 180 |
| tctaaagcaa | actcagtcaa | caacgtaaag | accaacttag | ccttgtgttt | cccacagtta | 240 |
| agtgaacaag | agcgtgacca | actggtttac | aaaacgcttt | atactgccgg | cgtatttact | 300 |
| cttagatttg | gcttggtctc | tttgcgttca | cccgaatggc | tgcaatcaaa | gtgtgacttt | 360 |
| gtaaactccg | aacagttgct | cgacctaact | gagcaaaatc | aaaaagtgat | tttattagtg | 420 |
| ccgcactctt | ggtcgattga | tatacctgcg | gtactacttg | cctcacaagg | cttacctgtt | 480 |
| tctgcgatgg | cgaaaagaca | gaaaaaccca | gtaacagact | ggctaatgca | tcgccaacgc | 540 |
| gtgcaatatg | gtggccgtgt | gtacgaacgc | tctggaggga | ttaaacccctt | catcaaatcg | 600 |
| attaaagacg | gttactttggg | ctactatcta | ccagaccagg | atcatggtgc | tgaactcagt | 660 |
| gaatttgtgg | acttttttcgc | gacgacgaag | gcaaccctgc | caggtctgac | aaaactggcg | 720 |

| | | |
|---|---|---|
| aaactgtcaa agtccaaagt aatcccgact tttgcctcac tggatccgga aactggtcgc | 780 |
| tttagtattg agttcatgcc tccactgacg cttcaggaaa ccgactgcga cgatgctcgc | 840 |
| tcactcaatg aagccattga gtactttgtg acgaaaaacc cagagcaata catgtggacc | 900 |
| ctgcgtctac tgcgtacaca ggcggatggc agtaacccat acagtgaaat gcgtgagcat | 960 |
| ggctttatta aagagaagtg a | 981 |

```
<210> SEQ ID NO 3
<211> LENGTH: 5395
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Allelic exchange plasmid to delete lpxL

<400> SEQUENCE: 3
```

| | | |
|---|---|---|
| caaccatcat cgatgaattg cttcgttaat acagatgtag gtgttccaca gggtagccag | 60 |
| cagcatcctg cgatgcagat ccggatgcca tttcattacc tctttctccg cacccgacat | 120 |
| agatccgaag atcagcagtt caacctgttg atagtacgta ctaagctctc atgtttcacg | 180 |
| tactaagctc tcatgtttaa cgtactaagc tctcatgttt aacgaactaa accctcatgg | 240 |
| ctaacgtact aagctctcat ggctaacgta ctaagctctc atgtttcacg tactaagctc | 300 |
| tcatgtttga acaataaaat taatataaat cagcaactta aatagcctct aaggttttaa | 360 |
| gttttataag aaaaaaaaga atatataagg ctttttaaagc ttttaaggtt taacggttgt | 420 |
| ggacaacaag ccagggatct gccatttcat tacctctttc tccgcacccg acatagatcc | 480 |
| ggaacataat ggtgcagggc gctgacttcc gcgtttccag actttacgaa acacggaaac | 540 |
| cgaagaccat tcatgttgtt gctcaggtcg cagacgtttt gcagcagcag tcgcttcacg | 600 |
| ttcgctcgcg tatcggtgat tcattctgct aaccagtaag gcaaccccgc cagcctagcc | 660 |
| gggtcctcaa cgacaggagc acgatcatgc gcacccgtgg ccaggaccca acgctgcccg | 720 |
| agatgcgccg cgtgcggctg ctggagatgg cggacgcgat ggatatgttc tgccaagggt | 780 |
| tggtttgcgc attcacaggt cgtggaaacg atagggacgg atctgctggc gaaggggga | 840 |
| tgtgctgcaa ggcgattaag ttgggtaacg ccagggtttt cccagtcacg acgttgtaaa | 900 |
| acgacggcca gtgaattaat tcttgaagac gaaagggcct cgtgatacgc ctattttat | 960 |
| aggttaatgt catgataata atggtttctt agagcttacg gccagcctcg cagagcagga | 1020 |
| ttcccgttga gcaccgccag gtgcgaataa gggacagtga agaaggaaca cccgctcgcg | 1080 |
| ggtgggccta cttcacctat cctgcccggc tgacgccgtt ggatacacca aggaaagtct | 1140 |
| acacgaaccc tttggcaaaa tcctgtatat cgtgcgaaaa aggatggata taccgaaaaa | 1200 |
| atcgctataa tgaccccgaa gcagggttat gcagcggaaa agatccgtcg atcgacccag | 1260 |
| gtggcacttt atgacaactt gacggctaca tcattcactt tttcttcaca accggcacgg | 1320 |
| aactcgctcg ggctggcccc ggtgcatttt ttaaataccc gcgagaaata gagttgatcg | 1380 |
| tcaaaaccaa cattgcgacc gacggtggcg ataggcatcc gggtggtgct caaaagcagc | 1440 |
| ttcgcctggc tgatacgttg gtcctcgcgc cagcttaaga cgctaatccc taactgctgg | 1500 |
| cggaaaagat gtgacagacg cgacggcgac aagcaaacat gctgtgcgac gctggcgata | 1560 |
| tcaaaattgc tgtctgccag gtgatcgctg atgtactgac aagcctcgcg tacccgatta | 1620 |
| tccatcggtg gatggagcga ctcgttaatc gcttccatgc gccgcagtaa caattgctca | 1680 |

```
agcagattta tcgccagcag ctccgaatag cgcccttccc cttgcccggc gttaatgatt    1740
tgcccaaaca ggtcgctgaa atgcggctgg tgcgcttcat ccgggcgaaa gaacccccgta   1800 ttggcaaata ttgacggcca gttaagccat tcatgccagt aggcgcgcgg acgaaagtaa    1860
acccactggt gataccattc gcgagcctcc ggatgacgac cgtagtgatg aatctctcct    1920
ggcgggaaca gcaaaatatc acccggtcgg caaacaaatt ctcgtccctg atttttcacc    1980
accccctgac cgcgaatggt gagattgaga atataacctt tcattcccag cggtcggtcg    2040
ataaaaaaat cgagataacc gttggcctca atcggcgtta aacccgccac cagatgggca    2100
ttaaacgagt atcccggcag caggggatca ttttgcgctt cagccatact tttcatactc    2160
ccgccattca gagaagaaac caattgtcca tattgcatca gacattgccg tcactgcgtc    2220
ttttactggc tcttctcgct aaccaaaccg gtaaccccgc ttattaaaag cattctgtaa    2280
caaagcggga ccaaagccat gacaaaaacg cgtaacaaaa gtgtctataa tcacggcaga    2340
aaagtccaca ttgattattt gcacggcgtc acactttgct atgccatagc attttttatcc   2400 ataagattag cggatcctac ctgacgcttt ttatcgcaac tctctactgt ttctccatac    2460 ccgtttttt gggaattcga gctctaagga ggttataaaa aatgcagttt aaggtttaca     2520
cctataaaag agagagccgt tatcgtctgt ttgtggatgt acagagtgat attattgaca    2580
cgccggggcg acggatggtg atcccctgg ccagtgcacg tctgctgtca gataaagtct     2640
cccgtgaact ttaccggtg gtgcatatcg gggatgaaag ctggcgcatg atgaccaccg      2700
atatggccag tgtgccggtc tccgttatcg gggaagaagt ggctgatctc agccaccgcg    2760
aaaatgacat caaaaacgcc attaacctga tgttctgggg aatataattg atattgcctt    2820
gctgcaactt ggttacgata agcagaaaga tatccaccat caccaatatg cttatggcat    2880
gttcagtagt gaatcgagtt atcgacagct gggtttaatc gatgagcttg gagactacag    2940
acactttcag cgtgaggttg ggaagatgct actcaatact cccgagccta ttgatatgca    3000 tatctattt gttatttctc aggagcatca caaagcggct aatacgctac attaatcctt     3060
tcactgtgcc gcaactgttt tcaatagcgt ggcacagttt tctagcttgt ttttccaaca    3120
cattttccta acacctttct ttatcgtcct ttccaaagcg tatgcgctgc attttcgggt    3180
aggaaaattc tatttattca aaagttcatg aaagtatgta ggtaatttac tctaaccaat    3240
gttaacgtgc tcaaatcttt tgtcgccttt acaatttaat tcgaagtcag tttgggttcc    3300
ctgtgtagtg tgtcgaagat ccataaaata cccgcgcttt aacttttttt gaagtgcaaa    3360
caatgataaa cgtttatgca attatcatta actttaatta cttatagtac cgttcgtata    3420
gcatacatta tacgaagtta ttgatgtccg gcggtgcttt tgccgttacg caccaccccg    3480
tcagtagctg aacaggaggg acagctgata gaaacagaag ccactggagc acctcaaaaa    3540
caccatcata cactaaatca gtaagttggc agcatcaccc gacgcacttt gcgccgaata    3600
aatacctgtg acgaagatc acttcgcaga ataaataaat cctggtgtcc ctgttgatac     3660
cgggaagccc tgggccaact tttggcgaaa atgagacgtt gatcggcacg taagaggttc    3720
caactttcac cataatgaaa taagatcact accgggcgta ttttttgagt tatcgagatt    3780
ttcaggagct aaggaagcta aatggagaa aaaatcact ggatatacca ccgttgatat      3840
atcccaatgg catcgtaaag aacattttga ggcatttcag tcagttgctc aatgtaccta    3900
taaccagacc gttcagctgg atattacggc ctttttaaag accgtaaaga aaataagca     3960 caagttttat ccggccttta ttcacattct tgcccgcctg atgaatgctc atccggaatt    4020
```

```
ccgtatggca atgaaagacg gtgagctggt gatatgggat agtgttcacc cttgttacac    4080
cgttttccat gagcaaactg aaacgttttc atcgctctgg agtgaatacc acgacgattt    4140
ccggcagttt ctacacatat attcgcaaga tgtggcgtgt tacggtgaaa acctggccta    4200
tttccctaaa gggtttattg agaatatgtt tttcgtctca gccaatccct gggtgagttt    4260
caccagtttt gatttaaacg tggccaatat ggacaacttc ttcgccccccg ttttcaccat    4320
gggcaaatat tatacgcaag cgacaaggt gctgatgccg ctggcgattc aggttcatca    4380
tgccgtctgt gatggcttcc atgtcggcag aatgcttaat gaattacaac agtactgcga    4440
tgagtggcag ggcggggcgt aattttttta aggcagttat tggtgccctt aaacgcctgg    4500
tgctacgcct gaataagtga taataagcgg atgaatggca gaaattcgaa agcaaattcg    4560
acccggtcgt cggttcaggg cagggtcgtt aaatagccgc ttatgtctat tgctggttta    4620
ccggtttatt gactaccgga agcagtgtga ccgtgtgctt ctcaaatgcc tgaggccagt    4680
ttgctcaggc tctccccgtg gaggtaataa ttgacgatat gatcatttat tctgcctccc    4740
agagcctgat aaaaacggtt aataacttcg tatagcatac attatacgaa cggtatgaat    4800
cgttttttagc tgttaatgct aagtagtggt ttaacatttt gaagccccca atcgttcacg    4860
attattgggg gcttttttatt tggataagtg aaacgatacg gggattgagc ctcttttctc    4920
tcgataggct agatcactga ggcctgtcat ttctaacctg tttaatctgc tattttttt     4980
acattcattg ggttgtatag tgaatgtact aagcttttct aacaatccgt ttttatcaag    5040
ccaacaccaa gaatcgagaa ctatgcccta tgtttgacga gttagctttt gccgggcttc    5100
tgtttagtcc gttggtggtt tttatgcctc ttgctttttt actgtcatgg agtacgcgtt    5160
ttgtgctgca taaatcaggc ttatacgcaa aactgtggaa ggcaccttgg tttgaagtca    5220
gcttgtatgt ctgttatctc gcgttagtca tttatctatt tgggagctaa tcatctatgg    5280
gaaaattcgt tcgcatctcc ctcactctta cgactttggt tattgccgtt attcttggcc    5340
attggatttg gcaacattat ctgtattcgc cttggacccg tgatggacga ataag         5395
```

<210> SEQ ID NO 4
<211> LENGTH: 5395
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Allelic exchange plasmid to delete lpxM

<400> SEQUENCE: 4

```
caaccatcat cgatgaattg cttcgttaat acagatgtag gtgttccaca gggtagccag      60
cagcatcctg cgatgcagat ccggatgcca tttcattacc tctttctccg cacccgacat     120
agatccgaag atcagcagtt caacctgttg atagtacgta ctaagctctc atgtttcacg     180
tactaagctc tcatgtttaa cgtactaagc tctcatgttt aacgaactaa accctcatgg     240
ctaacgtact aagctctcat ggctaacgta ctaagctctc atgtttcacg tactaagctc     300
tcatgtttga acaataaaat taatataaat cagcaactta aatagcctct aaggttttaa     360
gttttataag aaaaaaaaga atatataagg ctttttaaagc ttttaaggtt taacggttgt     420
ggacaacaag ccagggatct gccatttcat tacctctttc tccgcacccg acatagatcc     480
ggaacatatt ggtgcagggc gctgacttcc gcgtttccag actttacgaa acacggaaac     540
cgaagaccat tcatgttgtt gctcaggtcg cagacgtttt gcagcagcag tcgcttcacg     600
```

```
ttcgctcgcg tatcggtgat tcattctgct aaccagtaag gcaaccccgc cagcctagcc      660
gggtcctcaa cgacaggagc acgatcatgc gcacccgtgg ccaggaccca acgctgcccg      720
agatgcgccg cgtgcggctg ctggagatgg cggacgcgat ggatatgttc tgccaagggt      780
tggtttgcgc attcacaggt cgtggaaacg ataggacgg atctgctggc gaaaggggga       840
tgtgctgcaa ggcgattaag ttgggtaacg ccagggtttt cccagtcacg acgttgtaaa      900
acgacggcca gtgaattaat tcttgaagac gaaagggcct cgtgatacgc ctatttttat      960
aggttaatgt catgataata atggtttctt agagcttacg gccagcctcg cagagcagga     1020
ttcccgttga gcaccgccag gtgcgaataa gggacagtga agaaggaaca cccgctcgcg     1080
ggtgggccta cttcacctat cctgcccggc tgacgccgtt ggatacacca aggaaagtct     1140
acacgaaccc tttggcaaaa tcctgtatat cgtgcgaaaa aggatggata taccgaaaaa     1200
atcgctataa tgacccccgaa gcagggttat gcagcggaaa agatccgtcg atcgacccag    1260
gtggcacttt atgacaactt gacggctaca tcattcactt tttcttcaca accggcacgg     1320
aactcgctcg ggctggcccc ggtgcatttt ttaaataccc gcgagaaata gagttgatcg     1380
tcaaaaccaa cattgcgacc gacggtggcg ataggcatcc gggtggtgct caaaagcagc     1440
ttcgcctggc tgatacgttg gtcctcgcgc cagcttaaga cgctaatccc taactgctgg     1500
cggaaaagat gtgacagacg cgacggcgac aagcaaacat gctgtgcgac gctggcgata    1560
tcaaaattgc tgtctgccag gtgatcgctg atgtactgac aagcctcgcg tacccgatta    1620
tccatcggtg gatggagcga ctcgttaatc gcttccatgc gccgcagtaa caattgctca    1680
agcagattta tcgccagcag ctccgaatag cgcccttccc cttgcccggc gttaatgatt    1740
tgcccaaaca ggtcgctgaa atgcggctgg tgcgcttcat ccgggcgaaa gaacccgta    1800 ttggcaaata ttgacggcca gttaagccat tcatgccagt aggcgcgcgg acgaaagtaa    1860
acccactggt gataccattc gcgagcctcc ggatgacgac cgtagtgatg aatctctcct    1920
ggcgggaaca gcaaaatatc acccggtcgg caaacaaatt ctcgtccctg atttttcacc    1980
accccctgac cgcgaatggt gagattgaga atataacctt tcattcccag cggtcggtcg    2040
ataaaaaaat cgagataacc gttggcctca atcggcgtta aacccgccac cagatgggca    2100
ttaaacgagt atcccggcag caggggatca ttttgcgctt cagccatact tttcatactc    2160
ccgccattca gagaagaaac caattgtcca tattgcatca gacattgccg tcactgcgtc    2220
ttttactggc tcttctcgct aaccaaaccg gtaaccccgc ttattaaaag cattctgtaa    2280
caaagcggga ccaaagccat gacaaaaacg cgtaacaaaa gtgtctataa tcacggcaga    2340
aaagtccaca ttgattattt gcacggcgtc acactttgct atgccatagc atttttatcc    2400
ataagattag cggatcctac ctgacgcttt ttatcgcaac tctctactgt ttctccatac    2460
ccgttttttt gggaattcga gctctaagga ggttataaaa aatgcagttt aaggtttaca    2520
cctataaaag agagagccgt tatcgtctgt ttgtggatgt acagagtgat attattgaca    2580
cgccggggcg acgatggtg atcccctgg ccagtgcacg tctgctgtca gataaagtct      2640
cccgtgaact ttaccggtg gtgcatatcg gggatgaaag ctggcgcatg atgaccaccg     2700
atatggccca tgtgccggtc tccgttatcg gggaagaagt ggctgatctc agccaccgcg    2760
aaaatgacat caaaaacgcc attaacctga tgttctgggg aatataaagc acggtgagac    2820
cctatctcaa atcacgggct tccgttactt caatgtttac ggccctcgtg aagaccataa    2880
aggaagcatg gcatccgttg ccttccacct aaataaccag ctaaatgcag gtgaaaaccc    2940
gaaactcttc gcaggtagcg agacctttaa acgtgatttc gtttacgtcg gcgatgtatg    3000
```

```
caaagtaaat ctgtggttct tcgaaaatgg cgtatcaggc attttaact gtggcacagg      3060 acgcgcggag tcgtttgaag aggtcgcgaa agcggtgatc actcaccacg gaaaaggtga      3120
aatcgaaacg attcctttcc ctgagcatct aaaaggcgct taccaagagt tcactcaagc      3180
tgatctgact aagctacgct cagcaggctg cgacgtagaa ttcaaaacgg ttgcagaagg      3240
tgtctctgaa tacctagcca tccaaaatcg ctaagtatat ttgttcgcaa taatgaggtg      3300
gcggtgatta tgacctgcca ccttactca gcttcaatag cctgtatcat ttcctttatc      3360
tgcatttaaa tcactcgtct ccatacgcat aggtaactag actcccctac cgttcgtata      3420
gcatacatta tacgaagtta ttgatgtccg gcggtgcttt tgccgttacg caccaccccg      3480
tcagtagctg aacaggaggg acagctgata gaaacagaag ccactggagc acctcaaaaa      3540
caccatcata cactaaatca gtaagttggc agcatcaccc gacgcacttt gcgccgaata      3600
aatacctgtg acggaagatc acttcgcaga ataaataaat cctggtgtcc ctgttgatac      3660
cgggaagccc tgggccaact tttggcgaaa atgagacgtt gatcggcacg taagaggttc      3720
caactttcac cataatgaaa taagatcact accgggcgta ttttttgagt tatcgagatt      3780
ttcaggagct aaggaagcta aaatggagaa aaaaatcact ggatatacca ccgttgatat      3840
atcccaatgg catcgtaaag aacattttga ggcatttcag tcagttgctc aatgtaccta      3900
taaccagacc gttcagctgg atattacggc cttttaaag accgtaaaga aaataagca      3960 caagttttat ccggccttta ttcacattct tgcccgcctg atgaatgctc atccggaatt      4020
ccgtatggca atgaaagacg gtgagctggt gatatgggat agtgttcacc cttgttacac      4080
cgttttccat gagcaaactg aaacgttttc atcgctctgg agtgaatacc acgacgattt      4140
ccggcagttt ctacacatat attcgcaaga tgtggcgtgt tacggtgaaa acctggccta      4200
tttccctaaa gggtttattg agaatatgtt tttcgtctca gccaatccct gggtgagttt      4260
caccagtttt gatttaaacg tggccaatat ggacaacttc ttcgccccg ttttcaccat      4320 gggcaaatat tatacgcaag cgacaaggt gctgatgccg ctggcgattc aggttcatca      4380
tgccgtctgt gatggcttcc atgtcggcag aatgcttaat gaattacaac agtactgcga      4440
tgagtggcag ggcggggcgt aattttttta aggcagttat tggtgccctt aaacgcctgg      4500
tgctacgcct gaataagtga taataagcgg atgaatggca gaaattcgaa agcaaattcg      4560
acccggtcgt cggttcaggg cagggtcgtt aaatagccgc ttatgtctat tgctggttta      4620
ccggtttatt gactaccgga agcagtgtga ccgtgtgctt ctcaaatgcc tgaggccagt      4680
ttgctcaggc tctccccgtg gaggtaataa ttgacgatat gatcatttat tctgcctccc      4740
agagcctgat aaaacggtt aataacttcg tatagcatac attatacgaa cggtatatca      4800
acatgtcgaa aaacaaaatt ctaattattg gtccttcttg ggttggagat atggtgatgt      4860
cgcaatccct atacattgtt ttaaagcaac tgaaccctga agcgaaatt gatgtgattg      4920 cacccgggtg gtgtaaacca atcttagagc gtatgcctga ggtgaataag gccattgaaa      4980
tgccgattgg gcatggtgaa tttaaccttc tggggcggcg tgaaattggt aaaacgctgc      5040
gtgagaagaa atacgatcac gcttatatcc tgccaaaatc ggcgaaatcc gctctgatac      5100
cttggtttgc taacattcct cttcgcaccg gctggaaagg cgaaatgcgc tatgcttgc      5160 tgaatgacat tcgtcctaac atgaagtcgt tccaatacat ggtggagcgt tatgtggctt      5220
```

-continued

```
tggcttatcc acaatcggag atggtggact catcgtcact aggtggatta gagacgctgc    5280
cgcgccctcg cctagctatc aatactgaag agcaacaaac cactatccag aagtttaacc    5340
tcaataaaga acgctctatt attggcttgt gcccaggtgc agaatttggt ccggc         5395
```